United States Patent
Chang et al.

(10) Patent No.: US 7,960,614 B2
(45) Date of Patent: Jun. 14, 2011

(54) PLANT TRANSFORMATION AND SELECTION

(75) Inventors: Shujun Chang, N. Charleston, SC (US); Robert D. Thomas, Summerville, SC (US); Levis W. Handley, Takoma Park, MD (US); Marie B. Connett, Charleston, SC (US); Randy L. Hamilton, Charleston, SC (US)

(73) Assignee: Arborgen, LLC, Summerville, SC (US)

( * ) Notice: Subject to any disclaimer, the term of this patent is extended or adjusted under 35 U.S.C. 154(b) by 581 days.

(21) Appl. No.: 10/861,909

(22) Filed: Jun. 7, 2004

(65) Prior Publication Data

US 2006/0130185 A1 Jun. 15, 2006

Related U.S. Application Data

(60) Provisional application No. 60/476,222, filed on Jun. 6, 2003, provisional application No. 60/476,238, filed on Jun. 6, 2003.

(51) Int. Cl.
*C12N 15/29* (2006.01)
*C12N 15/52* (2006.01)
*C12N 15/82* (2006.01)

(52) U.S. Cl. ......... 800/300; 800/284; 800/294; 800/298

(58) Field of Classification Search .................. None
See application file for complete search history.

(56) References Cited

U.S. PATENT DOCUMENTS

| | | | |
|---|---|---|---|
| 5,034,323 A | 7/1991 | Jorgensen et al. | |
| 5,034,326 A | 7/1991 | Pullman et al. | |
| 5,036,007 A | 7/1991 | Gupta et al. | |
| 5,041,382 A | 8/1991 | Gupta et al. | |
| 5,231,020 A | 7/1993 | Jorgensen et al. | |
| 5,236,841 A | 8/1993 | Gupta et al. | |
| 5,283,184 A | 2/1994 | Jorgensen et al. | |
| 5,310,672 A | 5/1994 | Wann et al. | |
| 5,413,930 A | 5/1995 | Becwar et al. | |
| 5,491,090 A | 2/1996 | Handley, III et al. | |
| 5,506,136 A | 4/1996 | Becwar et al. | |
| 5,534,433 A | 7/1996 | Coke | |
| 5,534,434 A | 7/1996 | Coke | |
| 5,563,061 A | 10/1996 | Gupta | |
| 5,610,051 A | 3/1997 | Becwar et al. | |
| 5,821,126 A | 10/1998 | Durzan et al. | |
| 5,850,032 A | 12/1998 | Wann | |
| 5,952,486 A * | 9/1999 | Bloksberg et al. | 536/23.6 |
| 5,962,769 A | 10/1999 | Albertsen et al. | |
| 6,200,809 B1 | 3/2001 | Klimaszewska et al. | |
| 6,225,105 B1 | 5/2001 | Sathasivan et al. | |
| 6,255,559 B1 | 7/2001 | Cheah | |
| 6,271,016 B1 * | 8/2001 | Anderson et al. | 435/232 |
| 6,388,174 B1 * | 5/2002 | Wakasa et al. | 800/300 |
| 6,525,319 B2 | 2/2003 | Meglen et al. | |
| 6,606,568 B2 | 8/2003 | Meglen et al. | |
| 6,858,776 B1 * | 2/2005 | Podila et al. | 800/287 |
| 2002/0016981 A1 | 2/2002 | Flinn et al. | |
| 2002/0100083 A1 | 7/2002 | Connett-Porceddu et al. | |

FOREIGN PATENT DOCUMENTS

| | | |
|---|---|---|
| EP | 1 050 209 A2 | 4/2000 |
| JP | 2000-300274 A | 10/2000 |
| WO | WO 96/25504 A1 | 8/1996 |
| WO | WO 98/28430 * | 7/1998 |
| WO | WO 98/37212 | 8/1998 |
| WO | WO 99/48355 A1 | 9/1999 |
| WO | WO 99/49029 A1 | 9/1999 |
| WO | WO 99/53050 A1 | 10/1999 |
| WO | WO 00/12715 | 3/2000 |
| WO | WO 2004/108903 A2 | 12/2004 |

OTHER PUBLICATIONS

ABC Science Online Dec. 12, 2002.*
Sundararajan T. et al.; Biochem J.; Feb. 1957, 65(2).*
Odel J. et al. Plant Physiology 1990, (94); pp. 1647-1654.*
Lee Y, et al. Biochemistry, 2001; vol. 40, pp. 6836-6844.*
Tzfira et al., "Transgenic Populus tremula: a step-by-step protocol for its *Agrobacterium*-mediated transformation," *Plant Molecular Biology Reporter*, vol. 15, Kluwer Academic Publishers, Belgium, 1997, pp. 219-235.
International Search Report for PCT International Application No. PCT/US04/18024 mailed Apr. 18, 2007 (6 pgs.).
Gould et al. "Transformation and Regenerationof Loblolly Pine: Shoot Apex Inoculation with *Agrobacterium*", *Molecular Breeding*, 2002, vol. 10 (3), pp. 131-141.
Tang et al. "Genetic Transformation of Conifers and its Application in Forest Biotechnology", *Plant Cell Rep.*, Jun. 2003, vol. 22, pp. 1-15.
Tzfira et al., "*Agrobacerium* Rhizogenes-Mediation DNA Transfer in Pinus Halepensis Mill", *Plant Cell Rep.*, 1996, vol. 16, pp. 26-31.
English Translation of the Notice of Reasons for Rejection received for the corresponding Japanese Patent application No. 2006-515259, dated Mar. 17, 2010.
Bishop-Hurley, et. al., "Conifer genetic engineering:transgenic *Pinus radiata* (D. Don) and *Picea abies* (Karst) plants are resistant to the herbicide Buster", *Plant Cell Reports*, vol. 20, 2001, p. 235-243.
Guivareh, et al., "Localization of target cells and improvement of *Agrobacterium*-mediated transformation efficiency by direct acetosyringone pretreatment of carrot root discs", *Protoplasm*, vol. 174, 1993, pp. 10-18.
Harcourt, et al., "Insect- and herbicide-resistant transgenic eucalypts", *Molecular Breeding*, vol. 6, 2000, pp. 307-315.
Tang, W., "Additional virulence genes and sonication enhance *Agrobacterium tumefaciens*-mediated loblolly pine transformation", *Plant Cell Rep*, vol. 21, 2003, pp. 555-562.

(Continued)

Primary Examiner — Russell Kallis
(74) Attorney, Agent, or Firm — Foley & Lardner LLP

(57) ABSTRACT

The present invention relates to a genotype-independent method for transforming and selecting plant explants. The transformation method includes pre-culturing the explants in the presence of an *Agrobacterium* inducer and exposing the transformed explants to a shoot regeneration media that accelerates shoot development. Plants generated from this transformation method are provided. In particular, methods for obtaining transgenic *Eucalyptus* and pine cells and regenerating stably transformed *Eucalyptus* and pine trees are provided. The invention also provides media, methods, and plasmids for selecting and regenerating plants, particularly forest trees.

10 Claims, 14 Drawing Sheets

OTHER PUBLICATIONS

Tang, W. "Regeneration of transgenic loblolly pine (*Pinus taeda* L.), from zygotic embryos transformed with *Agrobacterium tumefaciens*", *Planta*, vol. 213, 2001, pp. 981-989.

Assaad et al., "Epigenetic repeat-induced gene silencing (RIGS) in *Arabidopsis*", Plant Molecular Biology, 1993, vol. 22, pp. 1067-1085.

Baucher et al., "Red xylem and Higher Lignin Extractability by Down-Regulating a Cinnamyl Alcohol Dehydrogenase in Poplar," Plant. Physiol., 1996, vol. 112, pp. 1479-1490.

Brasileiro et al., "An Alternative Approach for Gene Transfer in Trees Using Wild-type *Agrobacterium* strains," Plant Mol. Biol., Sep. 1991, vol. 17, No. 3, p. 441-452.

DeBlaere et al., "Efficient octopine Ti Plasmid-Derived Vectors for *Agrobacterium*-mediated Gene ransfer to Plants," Nucleic Acids Res., Jul. 11, 1985, vol. 13, No. 13, pp. 4777-4788.

DeBlock, Marc, "Factors Influencing the Tissue Culture and the *Agrobacterium tumefaciens*-mediated transformation of Hybrid Aspen and Poplar Clones," Plant Physiol., 1990, vol. 93,. pp. 1110-1116.

Fillatti et al., "Development of glyphosate-tolerate populus plants through expression of a mutant aroA gene from *Salmonella typhimurium*," Genetic Manipulation of Woody Plants, 1988, pp. 243-249.

Flavell, R.B., "Inactivation of gene expression in plants as a consequence of specific sequence duplication", Proc. Natl. Acad. Sci., Apr. 1994, vol. 91, pp. 3490-3496.

Gelvin, S.B., "*Agrobacterium*-Mediated Plant Transformation: the Biology behind the "Gene-Jockeying" Tool", Microbiology and Molecular Biology Reviews, Mar. 2003, vol. 67, No. 1, pp. 16-37.

GenBank Accessions No. 30685785, 2 pages, Feb. 23, 2005.
GenBank Accessions No. 30685789, 2 pages, Feb. 23, 2005.
GenBank Accessions No. 30693053, 3 pages, Jan. 25, 2005.
GenBank Accessions No. 3348125, 2 pages, Jul. 30, 2008.
GenBank Accessions No. 4256949, 2 pages, Feb. 9, 1999.

Grand, et al., "Inhibition of cinnamyl-alcohol-dehydrogenase activity and lignin synthesis in poplar (*Populus x euramericana* Dode) tissues by two organic compounds," *Planta*, (Berl.), 1985, vol. 163, pp. 232-237.

Harcourt et al., "Insect- and herbicide-resistant transgenic eucalypts", Molecular Breeding, 2000, vol. 6, pp. 307-315.

Ho et al., "*Agrobacterium tumefaciens*-mediated transformation of Eucalyptus camaldulensis and production of transgenic plants", Plant Cell Reports, 1998, vol. 17, pp. 675-680.

Huang et al., "*Agrobacterium rhizogenes*-mediated genetic transformation and regeneration of a conifer: larix decidua," In Vitro Cell Dev. Biol., Oct. 1991, vol. 27P, pp. 201-207.

Jefferson et al., GUS Fusions: Beta-glucuronidase as a Sensitive and Versatile Gene Fusion Marker in Higher Plants, The EMBO Journal, IRL Press Limited, Dec. 20, 1987, vol. 6, No. 13, pp. 3901-3907.

Kim et al., "*Agrobacterium*-mediated Transformation of Populus Species," USDA Forest Service Gen. Gech. Rep., RM-GTR-297, 1997, pp. 51-59.

Klopfenstein et al., "Transformation of Populus Hybrids to Study and Improve Pest Resistance," Silvae Genetica, 1993, vol. 42, No. 2-3, pp. 86-90.

Marita et al., "NMR characterization of lignins from transgenic poplars with suppressed caffeic acid O-methyltransferase activity", J. Chem. Soc., Perkin Trans. 1, 2001, pp. 2939-2945, The Royal Society of Chemistry.

Marx, J., "Interfering With Gene Expression", Science, May 26, 2000, vol. 288, pp. 1370-1372.

Minocha et al., "Tissue culture and genetic transformation in betula papyrifera and pupulus tremuloides," TAPPI Proceedings, 1986 Research and Development Conference, pp. 89-92.

Napoli, C., et al., "Introduction of a Chimeric Chalcone Synthase Gene into Petunia Results in Reversible Co-Suppression of Homologous Genes in trans," The Plant Cell, 1990, pp. 279-289, vol. 2.

Song et al., "Tissue Culture-Specific Expression of a Naturally Occurring Tobacco Feedback-Insensitive Anthranilate Synthase", Plant. Physiol., 1998, vol. 117, pp. 533-543.

Stam et al., "The Silence of Genes in Transgenic Plants", 1997, Annals of Botany, vol. 79, pp. 3-12.

Sullivan et al., "Transformation of Liquidambar styraciflua using *Agrobacterium tumefaciens*," Plant Cell Reports, 1993, vol. 12, pp. 303-306.

Tsai et al., "*Agrobacterium*-mediated transformation of quaking aspen (Populus tremuloides) and regeneration of transgenic plants," Plant Cell Reports, 1993, vol. 14, pp. 94-97.

Van Der Meer et al., "Antisense Inhibition of Flavonoid Biosynthesis in Petunia Anthers Results in Male Sterility", The Plant Cell, American Society of Plant Physiologists, Mar. 1992, vol. 4, pp. 253-262.

Von Arnold et al., "Regulation of Somatic Embryo Development in *Picea abides* by Abscisic Acid (ABA)", J. Plant Physio., 1988, vol. 132; pp. 164-169.

Wilde et al., "Expression of Foreign Genes in Transgenic Yellow-Poplar Plants," Plant Physiol., 1992, vol. 98, pp. 114-120.

Worrall et al., "Premature Dissolution of the Microsporocyte Callose Wall Causes Male Sterility in Transgenic Tobacco", The Plant Cell, Jul. 1992, vol. 4, pp. 759-771.

Yahiooui et al., "Comparative Efficiency of Different Constructs for Down Regulation of Tobacco Cinnamyl Alcohol Dehydrogenase", Phytochemistry, Elsevier Science Ltd., 1998, vol. 49, No. 2, pp. 295-306.

Ye et al., "Determination of $S_2$-fibril-angle and fiber-wall thickness by microscopic transmission ellipsometry", TAPPI Journal, Jun. 1997, vol. 80, No. 6, pp. 181-190.

\* cited by examiner

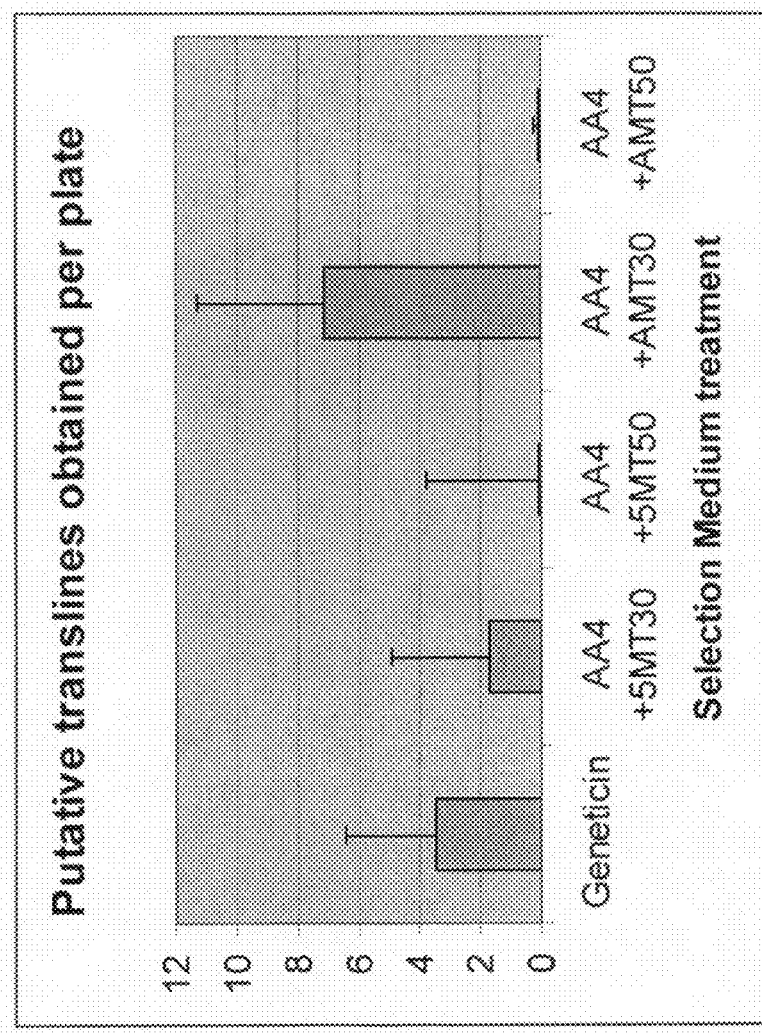

PLANT TRANSFORMATION AND SELECTION

BENEFIT OF PROVISIONAL APPLICATION

This application claims the benefit of U.S. Provisional Application No. 60/476,222, filed Jun. 6, 2003 and U.S. Provisional Application No. 60/476,238, filed Jun. 6, 2003.

FIELD OF THE INVENTION

The present invention relates to a genotype-independent method for transforming tree cells with foreign DNA and regenerating stably transformed trees therefrom. In particular, this invention teaches an *Agrobacterium*-mediated gene transfer method for transforming and regenerating transgenic plants from tree explants. The transformation process described herein utilizes a pre-culture medium that stimulates cell division and a shoot generation medium that accelerates shoot development. Plants generated from this transformation process are provided. In particular, the invention provides methods for increasing transformation efficiency and shoot regeneration from elite and recalcitrant clones. The invention also relates to media, methods, and plasmids for selecting and regenerating plants, particularly forest trees.

BACKGROUND

Plant genetic engineering has provided great potential for the improvement of commercially important plant species. In recent years, the genetic engineering of trees has gained momentum and finds particular application in the pulping and timber industries. Several established tree transformation systems exist for such species as sweetgum (Sullivan and Lagrinini 1993), European larch (Huang et al. 1991), yellow poplar (Wilde et al. 1992) and many *Populus* sp. (Minocha et al. 1986, Fillatti et al. 1988, De Block 1990, Brasileiro et al. 1992, Tsai et al. 1994). Species in the *Populus* genera have served as the model systems for the genetic engineering of trees (Kim et al. 1997). Various traits, such as insect resistance and herbicide tolerance, have been engineered into these tree species (Klopfenstein et al. 1993, De Block 1990). Thus, the potential for genetically engineering tree species is great for commercially important tree species, including *Eucalyptus*.

*Eucalyptus* plants are polygenus plants comprising more than five hundred species. *Eucalyptus* has a high growth rate, adapts to wide range of environments, and displays little susceptibility to insect damage. In addition to its exceptional growth properties, *Eucalyptus* trees provide the largest source of fibers for the paper industry. Fibers from hardwood species, such as *Eucalyptus*, are generally much shorter than fibers from softwoods, such as pine. The shorter fibers produced from *Eucalyptus* results in the production of pulp and paper with desirable surface characteristics, including smoothness and brightness, but low tear or tensile strength. As a timber, *Eucalyptus* provides tall, straight timber with a medium to high density. *Eucalyptus* timber is general-purpose; finds use in the plywood and particleboard industry, furniture industry; and provides a source of firewood and construction materials.

Most reports demonstrating transformation of *Eucalyptus* use *Eucalyptus* seedlings rather than elite genotypes obtained through breeding programs. For example, WO 99/48355 describes a method for transforming young leaf explants from seedlings of *E. grandis* and *E. camaldulensis*. Even though the transformation was successful, there are two main problems with the described method. First, the regeneration protocol works for seedling explants, but it does not work with explants from elite genotypes. Second, even with seedling explants and the claimed improvements, the transformation efficiency is limited to 2.2% or lower for cotyledon explants of the two species and the hypocotyl explants of *E. camaldulensis*. An improved transformation and regeneration protocol was reported for *E. camaldulensis* seedlings by Ho et al., *Plant Cell Reports* 17:675-680 (1998); but, the protocol was not repeatable even with *E. camaldulensis* seedlings. Thousands of explants were cultured, and transgenic callus lines were produced, but the number of shoots recovered was minimal. Hartcourt et al. *Molecular Breeding* 6:306-315 (2000) reported the transformation of *E. camaldulensis* seedlings with the insecticidal cry3A gene and the herbicide resistant bar gene. Although five herbicide resistant callus lines were regenerated from an unnumbered explants derived from fifty seedlings, one line was difficult to propagate in culture or in the greenhouse, and another line was proven to be an escape. Moreover, the line that was difficult to propagate was one of the two lines that were analyzed at molecular level, and it was the only line with a single insertion. These studies indicate that even when the recovery of transgenic *Eucalyptus* plants is possible, the low transformation efficiency precludes delivery of a desired gene into many genotypes. Thus, a need continues to exist for a genotype-independent method of *Eucalyptus* transformation and regeneration.

Although micropropagation of *Eucalyptus* seedlings has been performed, de novo shoot regeneration has been limited to seedlings instead of the selected or "elite" clones of commercially important *Eucalyptus* species. Elite genotypes, which arise through successive rounds of breeding, are valued for their combination of economically desirable traits. Unlike seedling transformation, which requires a large number of genotypes to ensure co-segregation of growth traits with the desired trait conferred by transgene expression, the transformation of elite clones would provide an efficient and advantageous system for genetically engineering tree species. Elite genotypes can be selected based on many years of clonal field test with a large number of starting genotypes. Like many other fast growing hardwood tree species, it takes years of field evaluation before relatively accurate predictions of a trait can be made for *Eucalyptus*. Therefore, if seedlings are used for genetic engineering, an even larger number of genotypes is needed for successful selection of a growth trait together with a desired trait conferred by transgene expression.

Both GB2298205 (WO/9625504) and EP 1050209 claimed the use of 1-(2-chlorl-4-pyridyl)-3-phehylurea or N-(2-chloro-4-pyridyl)-N'-phenylurea (4-PU or 4CPPU) as the primary cytokinin for regeneration of transgenic shoots. In both cases, antibiotics were used as selection agents. WO/9625504 demonstrates the transformation of explants from mature genotypes, but the inventors used seedling explants for *E. globules* and *E. nitens* to demonstrate transformation. EP 1050209 uses a vertical rotary culture system for inducing formation of transgenic primordia. Although transformation was demonstrated with rejuvenated explants from mature trees, the transformation efficiency was calculated based on transgenic callus production and there was no indication of the frequency for transgenic plant production. Since efficient de novo shoot regeneration is critical for genetic engineering, there is a need to develop a highly efficient regeneration system for the selection of clones from commercially important *Eucalyptus* species.

In addition to the need for an improved transformation system, there is a need for improved methods for selecting transformed plants. Most plant transformation protocols use antibiotic selection, incorporating an antibiotic into the selection media and an antibiotic resistance gene into the transformation gene construct. A common selection method uses nptII or hptII as a selectable marker and kanamycin or geneticin, or hygromycin, respectively, as a selection agent. While antibiotic selection provides a means for selecting transformed cells, it has several limitations. First, the incorporation of an antibiotic resistance gene in a transgenic organism is disfavored by the general public due to widespread concern about antibiotics and antibiotic resistance genes spreading from the transgenic organism into the environment. Second, antibiotic selectable markers provide no commercially desirable phenotype to the transformed plant, as they function only in the selection of transformed cells. Indeed, constitutive production of the antibiotic resistance protein may result in detriment to the value of the transformed plant in that it may divert a significant biomass from the commercially desirable phenotype.

To address these limitations, practitioners have investigated additional selectable markers for use in the production of transgenic plants. A popular replacement for the antibiotic selectable marker is herbicide resistance, such as that mediated by certain mutant genes encoding such enzymes as acetolactate synthase (ALS). The ALS enzyme catalyzes the first common step in a plant's biosynthetic pathway for producing the branched-chain amino acids valine, leucine and isoleucine. A number of effective and widely used herbicides target the ALS enzyme, including sulfonylureas, imidazolinones, and triazolopyrimidines.

Another type of resistance gene that has been explored for use in selection of transgenic plants shows resistance to a metabolic inhibitor that mimics natural feedback inhibition during production of a biosynthetic product, via a mutant gene that overcomes the metabolic inhibitor via constitutive overproduction of the product. An example of such a gene is anthranilate synthase (ASA), which mediates a critical step in the production of tryptophan, and is normally subject to feedback inhibition by tryptophan. Besides acting as selectable markers, such genes can confer a desirable growth phenotype on the transgenic plant it if the biochemical product, in this case tryptophan, is normally a limiting factor to the plant's growth.

While non-antibiotic selectable marker genes overcome some of the problems associated with using antibiotic resistance markers, the use of non-antibiotic selectable marker genes has not been a panacea for plant transformations. One problem associated with these markers is a high rate of false positives. Thus, practitioners are forced to evaluate many transformants to identify a true positive. Such excessive screening greatly increases the time and cost associated with creating transgenic plants.

Accordingly, there is a need for improved methods of selecting transformed plants.

Accordingly, there is a need to increase the frequency of transforming *Eucalyptus* cells and regenerating stably transformed plants from clones of elite germplasm.

SUMMARY OF THE INVENTION

Contemplated in the present invention is a method for transforming at least one cell of a tree explant with a foreign DNA, comprising (i) pre-culturing a tree explant on a medium comprising an inducer of *Agrobacterium*; (ii) exposing said explant to an *Agrobacterium* strain containing a transformation vector carrying said foreign DNA; (iii) selecting a transformed explant, wherein said foreign DNA is transferred to at least one cell of said transformed explant; and (iv) regenerating said transformed explant to produce a complete plant. Preferably, the inducer of *Agrobacterium* is acetosyringone and the concentration of said acetosyringone is from about 10 to about 400 mg/l. Also preferred, the concentration of said acetosyringone is from about 5 to about 200 mg/l and the medium further comprises auxin and/or cytokinin. The invention contemplates a pre-culturing step comprises culturing a plant explant on a nutrient medium before *Agrobacterium* transformation. The pre-culture medium comprises an inducer of *Agrobacterium*, such as acetosyringone. n one embodiment, the explant is pre-cultured in the dark from about 1 to about 6 days. Preferably, the explant is pre-cultured for about 4 days. In one embodiment, the pre-culture medium may optionally comprise plant growth regulators, including auxin and cytokinin In another embodiment, the auxin is selected from the group consisting of NAA, 2,4-D, IBA, and IAA. In one embodiment, the concentration range of any one of NAA, 2,4-D, IBA, and IAA is from about 0.1 to about 10 mg/l. Preferably, the concentration range is from about 0.2 to about 5 mg/l. More preferably, the concentration range is from about 0.2 to about 3 mg/l.

In another embodiment, the cytokinin is selected from the group consisting of zeatin, kinetin, and BA. In one embodiment, the concentration range of any one of said zeatin, kinetin, and BA is from about 0.25 to about 15 mg/l. Preferably, the concentration range is from about 1 to about 10 mg/l. More preferably, the concentration range is from about 1 to about 6 mg/l.

In another embodiment, the explant is at least one of a leaf a petiole, an internodal tissue, floral tissue, embryogenic tissue, or embryogenic culture.

In one embodiment, the tissues are selected independent of age or developmental stage.

In another embodiment, the method is genotype-independent.

In another embodiment, all of the cells of said transformed explant comprise the foreign DNA.

In one embodiment, the explant is selected from the group consisting of a *Eucalyptus* or Pine species.

Also described in the present invention is a transgenic *Eucalyptus* plant, wherein said plant is a non-chimaeric transgenic plant. Preferably, the transgenic *Eucalyptus* plant is a non-chimaeric *E. grandis*, a non-chimaeric *E. nitens*, a non-chimaeric *E. globulus*, a non-chimaeric *E. dunnii*, a non-chimaeric *E. saligna*, a non-chimaeric *E. occidentalis*, or hybrids thereof.

In a related vein, the present invention discloses a method for producing a non-chimaeric tree, comprising (i) pre-culturing an explant on a medium comprising an inducer of *Agrobacterium*; (ii) exposing said explant to an *Agrobacterium* strain harboring a vector capable of transferring a gene to a plant cell; (iii) selecting a transformed explant; and (iv) growing said explant to produce a non-chimaeric tree.

In one embodiment, the method is genotype-independent.

Also described is a method for producing a transgenic tree, comprising
(i) pre-culturing said explant on a medium comprising an inducer of *Agrobacterium;*
(ii) transforming said explant with an *Agrobacterium* strain harboring a vector capable of transferring a gene to a plant cell; (iii) selecting a transformed explant; and
(iv) regenerating said explant to produce a transgenic plant.

In one embodiment, the method is genotype-independent.

In another embodiment, the method produces a transgenic *Eucalyptus* plant.

In another embodiment, the method produces a transgenic *Eucalyptus* plant having a herbicide resistance gene and a foreign gene.

In another aspect, the invention provides a transgenic *Eucalyptus* plant, wherein the plant is stably transformed with a foreign DNA and is capable of transmitting said foreign DNA to progeny. In some embodiments, the transgenic *Eucalyptus* plant is *E. grandis* and its hybrids, *E. nitens* and its hybrids, *E. globulus* and its hybrids, *E. dunnii* and its hybrids, *E. saligna* and its hybrids, and *E. occidentalis* and its hybrids.

In another aspect, the invention provides a plant medium composition comprising a sulfyonyl herbicide and a casein hydrolysate-like compound, wherein the compound is substantially free of branched chain amino acids.

In a related vein, the invention provides a method for producing a transgenic plant, comprising (i) pre-culturing said explant on a medium comprising an inducer of *Agrobacterium*; (ii) exposing said explant to an *Agrobacterium* strain harboring a vector capable of transferring a gene to a plant cell; (iii) selecting a transformed explant on a culture medium comprising a sulfonylurea or imidazolinone herbicide and a casein hydrolysate-like compound, wherein said compound is substantially free of branched chain amino acids and does not interfere with sulfonylurea or imidazolinone selection; and (iv) regenerating a whole plant from said explant.

In another aspect, the invention provides a transgenic *Eucalyptus* plant, *E. occidentalis*. Also described is a transgenic *Eucalyptus* plant, *E. dunnii.*, an *E. occidentalis* plant comprised of at least one cell stably transformed with a foreign DNA, an infertile *E. dunnii* transformed with a foreign DNA, and a stably transformed *E. saligna* plant, wherein said plant is capable of transmitting foreign DNA to progeny.

In another aspect, the invention provides tree pre-culture medium comprising an inducer of *Agrobacterium*. Also described is a *Eucalyptus* pre-culture medium comprising an inducer of *Agrobacterium*.

In another aspect, the invention provides a method for obtaining wood pulp, comprising (i) culturing a tree explant on a pre-culture medium comprising an inducer of *Agrobacterium*; (ii) exposing said explant to an *Agrobacterium* strain containing a transformation vector carrying said foreign DNA; (iii) selecting a transformed explant, wherein said foreign DNA is transferred to at least one cell of said transformed explant; (iv) regenerating said transformed explant to produce a complete plant; and (v) obtaining wood pulp from said plant.

In another aspect, the invention provides a method for obtaining lumber, comprising (i) culturing a tree explant on a pre-culture medium comprising an inducer of *Agrobacterium*; (ii) exposing said explant to an *Agrobacterium* strain containing a transformation vector carrying said foreign DNA; (iii) selecting a transformed explant, wherein said foreign DNA is transferred to at least one cell of said transformed explant; (iv) regenerating said transformed explant to produce a complete plant; and (v) obtaining lumber from said plant.

In another aspect, the invention provides a method for obtaining paper, comprising (i) culturing a tree explant on a pre-culture medium comprising an inducer of *Agrobacterium*; (ii) exposing said explant to an *Agrobacterium* strain containing a transformation vector carrying said foreign DNA; (iii) selecting a transformed explant, wherein said foreign DNA is transferred to at least one cell of said transformed explant; (iv) regenerating said transformed explant to produce a complete plant; and (v) obtaining paper from said plant.

In another aspect, the invention provides a method for obtaining oil, comprising (i) culturing a tree explant on a pre-culture medium comprising an inducer of *Agrobacterium*; (ii) exposing said explant to an *Agrobacterium* strain containing a transformation vector carrying said foreign DNA; (iii) selecting a transformed explant, wherein said foreign DNA is transferred to at least one cell of said transformed explant; (iv) regenerating said transformed explant to produce a complete plant; and (v) obtaining oil from said plant.

In a related vein, the invention provides a method for obtaining wood pulp, comprising (i) pre-culturing an explant on a medium comprising an inducer of *Agrobacterium*; (ii) exposing said explant to an *Agrobacterium* strain harboring a vector capable of transferring a gene to a plant cell; (iii) selecting a transformed explant on a culture medium comprising a sulfonylurea or imidazolinone herbicide and a casein hydrolysate-like compound, wherein said compound is substantially free of branched chain amino acids and does not interfere with sulfonylurea or imidazolinone selection; (iv) regenerating a whole plant from said explant; and and (v) obtaining wood pulp from said plant.

In another aspect, the invention provides a method for obtaining lumber, comprising (i) pre-culturing an explant on a medium comprising an inducer of *Agrobacterium*; (ii) exposing said explant to an *Agrobacterium* strain harboring a vector capable of transferring a gene to a plant cell; (iii) selecting a transformed explant on a culture medium comprising a sulfonylurea or imidazolinone herbicide and a casein hydrolysate-like compound, wherein said compound is substantially free of branched chain amino acids and does not interfere with sulfonylurea or imidazolinone selection; (iv) regenerating a whole plant from said explant; and and (v) obtaining lumber from said plant.

In another aspect, the invention provides a method for obtaining paper, comprising (i) pre-culturing an explant on a medium comprising an inducer of *Agrobacterium*; (ii) exposing said explant to an *Agrobacterium* strain harboring a vector capable of transferring a gene to a plant cell; (iii) selecting a transformed explant on a culture medium comprising a sulfonylurea or imidazolinone herbicide and a casein hydrolysate-like compound, wherein said compound is substantially free of branched chain amino acids and does not interfere with sulfonylurea or imidazolinone selection; (iv) regenerating a whole plant from said explant; and and (v) obtaining paper from said plant.

In another aspect, the invention provides a method for obtaining oil, comprising (i) pre-culturing an explant on a medium comprising an inducer of *Agrobacterium*; (ii) exposing said explant to an *Agrobacterium* strain harboring a vector capable of transferring a gene to a plant cell; (iii) selecting a transformed explant on a culture medium comprising a sulfonylurea or imidazolinone herbicide and a casein hydrolysate-like compound, wherein said compound is substantially free of branched chain amino acids and does not interfere with sulfonylurea or imidazolinone selection; (iv) regenerating a whole plant from said explant; and and (v) obtaining oil from said plant.

Other objects, features and advantages of the present invention will become apparent from the following detailed description. The detailed description and specific examples, while indicating preferred embodiments, are given for illustration only since various changes and modifications within the spirit and scope of the invention will become apparent to those skilled in the art from this detailed description. Further, the examples demonstrate the principle of the invention and cannot be expected to specifically illustrate the application of this invention to all the examples where it will be obviously useful to those skilled in the prior art.

BRIEF DESCRIPTION OF THE DRAWINGS

FIG. 12 demonstrates the ability of 5MT and AMT to act as selection agents when used with the selectable marker ASA2 to identify transgenic plants.

DETAILED DESCRIPTION OF THE INVENTION

Figure 1:
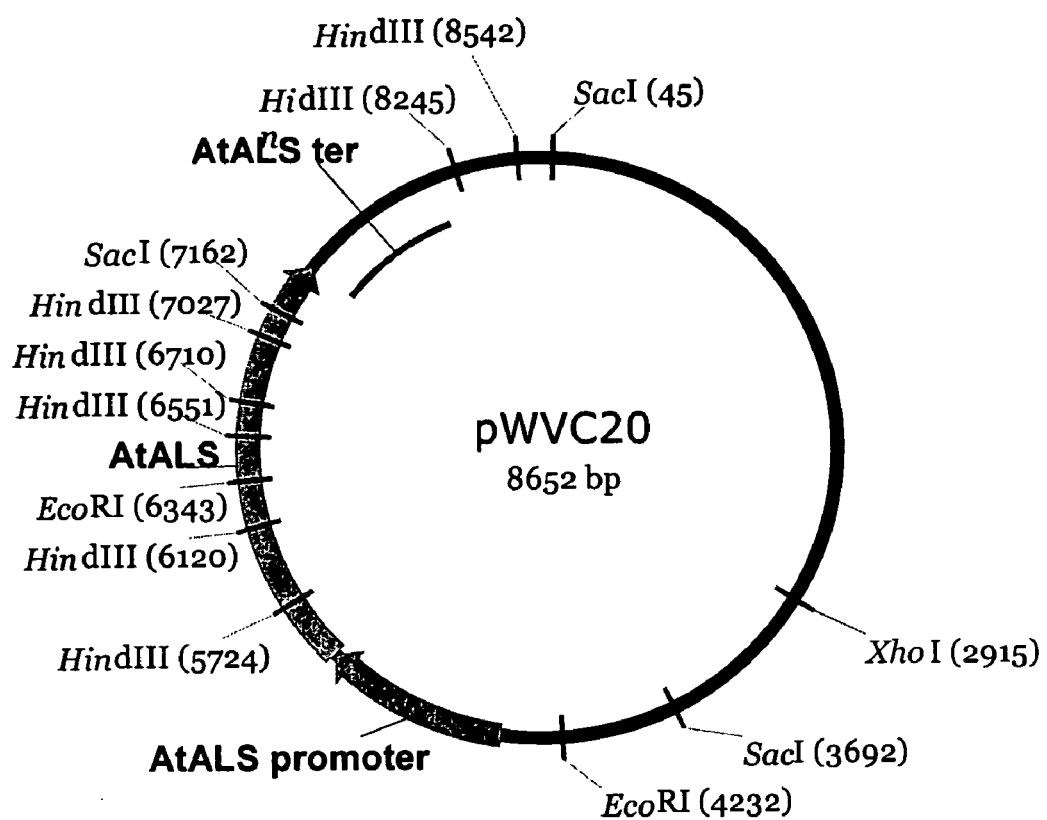
FIG. 1 provides a schematic representation of the vector pWVC20.

The methods of the present invention for genotype-independent tree transformation overcome the low transformation efficiencies obtained from the transformation of elite genotypes. In its broadest aspect, the methods relate to increasing the efficiencies of transformation and shoot regeneration from tree explants. Increases in transformation efficiency are accomplished by pre-culturing the explants on a medium that stimulates cell division. The shoot regeneration frequency of the transformed explants is improved by culturing the explants on a medium that promotes shoot regeneration.

The present invention provides media compositions useful for selecting transgenic plants. The media can be used to culture any plant cell that has been transformed with one or more selectable markers that alter amino acid metabolism. The inventive media and methods are particularly useful for selecting transgenic forest trees.

In one embodiment, the media comprises a selection agent that targets ALS and a derivative of casein hydrolysate that is substantially free of branched chain amino acids. The derivative also can possess elevated concentrations of amino acids such as glutamine and arginine, important amino acids for growing and maintaining regenerable cells of certain plants in plant tissue culture.

In another embodiment, the media comprises a tryptophan analog as a selection agent that targets anthranilate synthase, and a derivative of casein hydrolysate that is substantially free of tryptophan. The derivative also can possess elevated concentrations of amino acids such as glutamine and arginine, important amino acids for growing and maintaining regenerable cells of certain plants in plant tissue culture.

In the description that follows, a number of scientific and technical terms are used extensively. Unless defined otherwise, all technical and scientific terms used herein share the same meaning as commonly understood by one of ordinary skill in the art to which this invention belongs. The following definitions are provided to facilitate understanding of the invention.

Abaxial, as used herein, refers to the lower side of a leaf.

*Agrobacterium* inducer refers to a molecule that induces expression of *Agrobacterium* virulence genes that code for products that control excision and delivery of the T-DNA into the host plant nucleus. In the present description, *Agrobacterium* inducers were added to both the pre-culture medium and the *Agrobacterium* culture medium. In this invention, *Agrobacterium* inducers include, but are not limited to, phenolic compounds, such as acetosyringone. Addition of an inducer improves *Agrobacterium* infection frequency and consistency.

*Agrobacterium*-mediated transformation is a method by which DNA is stably inserted into the genome of a plant cell through the use of the Ti (tumor-inducing) plasmid from *Agrobacterium tumefaciens*. A small portion of the Ti plasmid, known as the T-DNA, is incorporated into the nucleus of the host plant cell. Alternatively, the Ri plasmid from *Agrobacterium rhizogenes* may be used for transformation. In *Agrobacterium*-mediated transformation, the gene(s) or DNA intended for plant introduction is positioned between the left and right borders of the T-DNA.

Antioxidant, as used herein, refers to a compound that minimizes the exudation of phenolic materials from a plant explant. In the present invention, ascorbic acid may be used as an antioxidant.

In the present description, the term auxin encompasses a class of plant growth regulators that are characterized principally by their capacity to stimulate cell division in excised plant tissues. In addition to their role in cell division and cell elongation, auxins influence other developmental processes, including root initiation. In the present invention, auxin and auxin-type growth regulators include, but are not limited to, naphthaleneacetic acid (NAA), 2,4-Dichlorophenoxy acetic acid (2,4-D), indole-3-butyric acid (IBA), and indole-3-acetic acid (IAA).

Casein hydrolysate-like compound refers to a composition that is structurally and functionally related to casein hydrolysate. In the context of the phrase "casein hydrolysate-like compound, the term denotes a compound that has a similar composition of amino acids as casein hydrolysate, and achieves the same function as casein hydrolysate, but differs in one or more components. For example, a casein hydrolysate-like compound can possess elevated concentrations of amino acids such as glutamine and arginine, important amino acids for growing and maintaining regenerable cells of certain plants in plant tissue culture.

A cloning vector is a genetic element, such as a plasmid, cosmid, or bacteriophage, that has the capability to replicate autonomously in a host cell. Cloning vectors comprise one or a small number of restriction endonuclease recognition sites in which foreign DNA sequences can be inserted in a determinable orientation and a marker gene that encodes a product suitable for the identification and selection of cells transformed with the cloning vector. Marker genes include genes whose products confer antibiotic or herbicide resistance. The insertion of a foreign DNA sequence into a cloning vector does not interfere with an essential biological function of the cloning vector or the marker gene.

Cytokinin refers to a class of plant growth regulators that are characterized by their ability to stimulate cell division and shoot organogenesis in tissue culture. In the present invention, cytokinins include, but are not limited to, $N^6$-benzylaminopurine (BAP), $N^6$-benzyladenine (BA), zeatin, kinetin, thiadiazuron (TDZ), 2-isopentenyladenine (2ip), and 4-CPPU (N-(2-chloro-4-pyridyl)-N'-phenylurea)).

Derivative refers to a substance that is structurally and functionally related to another substance. In the context of the phrase "derivative of casein hydrolysate," the term denotes a substance that has a similar composition of amino acids as casein hydrolysate, and achieves the same function as casein hydrolysate, but differs in one or more components. For example, a derivative of casein hydrolysate may have more arginine and/or less valine than a typical casein hydrolysate.

As used herein, elite genotype refers to commercially important genotypes obtained and selected for through successive breeding programs.

The term explant refers to plant tissue that is a target for transformation. Preferred explants comprise leaf, petiole, floral tissue, internodal tissues, and embryogenic tissues harvested from plants grown in vivo and/or in vitro.

The term expression refers to the biosynthesis of a gene product. For example, expression of a gene involves transcription of the DNA sequence into mRNA and translation of the mRNA into one or more polypeptides. The RNA generated may code for a protein or polypeptide or may code for an RNA interfering, or antisense molecule.

An expression vector is a genetic element comprising a gene sequence that is expressed in a host cell. Typically, the expression of the gene sequence is controlled by several regulatory elements, including constitutive and inducible promoters, tissue-preferred regulatory elements, and enhancers. Such a gene is said to be "operably linked" to the regulatory elements.

A foreign DNA is DNA isolated from another species or from the species of interest and re-introduced into the same species. The DNA may be a structural gene, an antisense gene, DNA fragments, etc.

A gene is a heritable DNA sequence that is transcribed into messenger RNA (mRNA) which is then translated into a sequence of amino acids characteristic of a polypeptide.

A non-chimaeric transgenic plant is the product of a transformation event wherein essentially all of the cells are transformed and a foreign DNA is transferred to progeny.

Operably linked describes combining two or more molecules in such a fashion that in combination they function properly in a plant cell. For instance, a promoter is operably linked to a structural gene when the promoter controls transcription of the structural gene.

As used herein, plant is any of various photosynthetic, eukaryotic, multicellular organisms of the kingdom Plantae characteristically producing embryos, containing chloroplasts, and having cellulose cell walls. As part of a plant, a plant tissue may be treated according to the methods of the present invention to produce a transgenic plant. Many suitable plant tissues can be transformed according to the present invention and include, but are not limited to, somatic embryos, pollen, leaves, stems, calli, stolons, microtubers, and shoots. Thus, the present invention envisions the transformation of angiosperm and gymnosperm plants such as turfgrass, wheat, maize, rice, barley, oat, sugar beet, potato, tomato, tobacco, alfalfa, lettuce, carrot, strawberry, cassava, sweet potato, geranium, soybean, oak, pine, fir, acacia, eucalyptus, walnut, and palm. According to the present invention plant tissue also encompasses plant cells. Plant cells include suspension cultures, callus, embryos, meristematic regions, callus tissue, leaves, roots, shoots, gametophytes, sporophytes, pollen, seeds and microspores. Plant tissues may be at various stages of maturity and may be grown in liquid or solid culture, or in soil or suitable media in pots, greenhouses or fields. A plant tissue also refers to any clone of such a plant, seed, progeny, propagule whether generated sexually or asexually, and descendents of any of these, such as cuttings or seed. Of particular interest are conifers such as pine, fir and spruce, monocots such as Kentucky bluegrass, creeping bentgrass, maize, and wheat, and dicots such as *Eucalyptus*, Acacia, aspen, Sweetgum, poplar, cotton, tomato, lettuce, *Arabidopsis*, tobacco, and geranium.

Plant promoter is a promoter capable of initiating transcription in plant cells whether or not its origin is a plant cell. Exemplary plant promoters include, but are not limited to, those that are obtained from plants, plant viruses, and bacteria such as *Agrobacterium* or *Rhizobium* which comprise genes expressed in plant cells. Examples of promoters under developmental control include promoters that preferentially initiate transcription in certain tissues, such as leaves, roots, or seeds. Such promoters are referred to as tissue-preferred promoters. Promoters which initiate transcription only in certain tissue are referred to as tissue-specific promoters. A cell type-specific promoter primarily drives expression in certain cell types in one or more organs, for example, vascular cells in roots or leaves. An inducible or repressible promoter is a promoter which is under environmental control. Examples of environmental conditions that may effect transcription by inducible promoters include anaerobic conditions or the presence of light. Tissue specific, tissue preferred, cell type specific, and inducible promoters constitute the class of non-constitutive promoters. A constitutive promoter is a promoter which is active under most environmental conditions, and in most plant parts.

Pre-culture medium, as used herein, is the nutrient medium upon which plant explants are cultured prior to transformation with *Agrobacterium* and is needed for increasing transformation efficiency and plant regeneration. The pre-culture medium comprises an inducer of *Agrobacterium*, such as acetosyringone. The pre-culture medium may optionally comprise plant growth regulators, including auxin and cytokinin.

Progeny: a "progeny" of the present invention, such as the progeny of a transgenic plant, is one that is born of, begotten by, or derived from a plant or the transgenic plant. Thus, a "progeny" plant, i.e., an "F1" generation plant is an offspring or a descendant of the transgenic plant produced by the inventive methods. A progeny of a transgenic plant may contain in at least one, some, or all of its cell genomes, the desired polynucleotide that was integrated into a cell of the parent transgenic plant by the methods described herein. Thus, the desired polynucleotide is "transmitted" or "inherited" by the progeny plant. The desired polynucleotide that is so inherited in the progeny plant may reside within a T-DNA construct, which also is inherited by the progeny plant from its parent. The term "progeny" as used herein, also may be considered to be the offspring or descendants of a group of plants.

Shoot regeneration medium is the inventive medium designed to regenerate transgenic shoots. The shoot regeneration medium comprises inorganic salts, a mixture of amino acids and vitamins, an antioxidant, organic nitrogen, and plant growth regulators.

Somatic embryogenesis is a method of clonal propagation wherein the embryo develops from vegetative or somatic tissue rather than as a product of gametic fusion.

Stably transformed refers to a transgenic plant that is capable of transmitting foreign DNA to progeny.

Structural gene is a DNA sequence that is transcribed into messenger RNA (mRNA) which is then translated into a sequence of amino acids characteristic of a specific polypeptide.

Substantially free refers to the relative absence of a first compound from a second compound. The term denotes that less than 10%, 5%, 4%, 3%, 2%, 1% or even 0% of a first compound can be detected in a second compound.

A transgenic plant is a plant comprising foreign DNA. In this invention, a transgenic plant is derived from *Agrobacterium*-mediated transformation. Preferably, the transgenic plant is fertile and capable of transmitting the foreign DNA to progeny plant through sexual reproduction.

Transcription and translation terminators: The expression DNA constructs of the present invention typically have a transcriptional termination region at the opposite end from the transcription initiation regulatory region. The transcriptional termination region may be selected, for stability of the mRNA to enhance expression and/or for the addition of polyadenylation tails added to the gene transcription product.

Tree, as used herein, refers to any perennial vegetation that accumulates a wood core. Trees include angiosperms and gymnosperm species. Examples of trees include poplar, *Eucalyptus*, Douglas fir, pine, sugar and Monterey, nut trees, e.g., walnut and almond, fruit trees, e.g., apple, plum, citrus and apricot, and hardwood trees, such as ash, birch, oak, and teak. Of particular interest are conifers such as pine, fir, spruce, *Eucalyptus*, Acacia, aspen, Sweetgum, and poplar.

The present invention provides genotype-independent methods for transforming tree explants and generating transgenic progeny therefrom. The methods of the present invention contemplate pre-culturing tree explants in the presence of an *Agrobacterium* inducer. The methods of the present invention further envision culturing the transformed explants on a shoot regeneration medium comprising amino acids, vitamins, plant growth regulators, glucose, and an antioxidant.

The methods of the instant invention provide a genotype-independent method of *Eucalyptus* explant transformation and shoot regeneration. Any *Eucalyptus* explant may be transformed by the methods of the instant invention, including *Eucalyptus* trees grown in natural environments and *Eucalyptus* explants clonally propagated. The explant may be selected from any *Eucalyptus* species, including *Eucalyptus alba, Eucalyptus bancroftii, Eucalyptus botryoides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus nova-angelica, Eucalyptus obliqua, Eucalyptus occidentalis, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo*, and *Eucalyptus youmanni*.

Also preferred, the target plant is selected from the group consisting of *Pinus banksiana, Pinus brutia, Pinus caribaea, Pinus clasusa, Pinus contorta, Pinus coulteri, Pinus echinata, Pinus eldarica, Pinus elliotii, Pinus jeffreyi, Pinus lambertiana, Pinus massoniana, Pinus monticola, Pinus nigra, Pinus palustris, Pinus pinaster, Pinus ponderosa, Pinus radiata, Pinus resinosa, Pinus rigida, Pinus serotina, Pinus strobus, Pinus sylvestris, Pinus taeda, Pinus virginiana, Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Juniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata*.

In particular, the transgenic plant may be *Eucalyptus grandis* or its hybrids, *Pinus radiata, Pinus taeda* L (loblolly pine) or its hybrids, *Populus nigra, Populus deltoides, Populus alba*, or *Populus hybrids, Acacia mangium*, or *Liquidamber styraciflua*.

The methods of the instant invention contemplate the transformation of *Eucalyptus* explants obtained from a stock culture of elite *Eucalyptus* genotypes. Micropropagated shoot cultures may be generated by harvesting newly flushed apical or axillary shoots and surface sterilizing the tissues in a sterilization solution. Sterilization solutions, such as 1-5% bleach solution, are known in the art and repeated rinsing with sterile, distilled water can be performed. *Eucalyptus* stock cultures can be maintained as shoot clusters on a maintenance medium comprising inorganic salts, carbon sources, vitamins, and cytokinins. In the present invention, stock cultures are maintained on *Eucalyptus* Maintenance (EM) medium (Table 1) comprising Woody Plant Medium (WPM) salts (Loyd and McCown, 1980) and $N^6$-benzyladenine (BA). Alternatively, other salt media, such as MS medium (Murashige and Skoog 1962) or Lepoivre medium, may be used.

TABLE 1

*Eucalyptus* Maintenance Medium (EM medium)

| Medium Components | Amount per Liter of Medium |
|---|---|
| WPM salts | 1 package (Sigma) |
| Ca(NO$_3$)$_2$•4H$_2$O | 3.7 g |
| MgSO$_4$•4H$_2$O | 0.37 g |
| Nicotinic Acid | 0.5 mg |
| Thiamine•HCl | 0.5 mg |
| Pyridoxin•HCl | 0.5 mg |
| D-Pantothenic Acid | 1.0 mg |
| Myo-inositol | 0.1 g |
| BA | 0.1-1 mg |
| Bacto-agar | 5-8 g |

The present invention provides a method of genotype-independent transformation. The methods of the present invention teach the transformation of explants independent of age and developmental stage. Tree explants obtained from the stock culture can be used for transformation. Tree explants may be selected from one of more of leaf, petiole, internodal, and floral tissues. In the present invention, leaf explants are selected due to their abundant supply and ease of transformation. The tip portion of leaves may be removed or punctured with a forcep to increase the number of wounded cells. In the instant application, leaf explants are placed on the pre-culture medium abaxial side down.

In the instant application, plant explants are cultured on a pre-culture medium. A pre-culture medium is a nutrient medium upon which plant explants are cultured before *Agrobacterium* transformation. Specifically, the inventive pre-culture medium increases transformation efficiency and plant regeneration. The pre-culture medium comprises an inducer of *Agrobacterium*, such as acetosyringone. Alternatively, other *Agrobacterium* inducers may be used, such as hydroxyphenylpropanoids, phenolic compounds, and coniferin. Woody Plant Medium (WPM) salts (Loyd and McCown, 1980) were used in the present invention; however, other salt media, such as MS medium (Murashige and Skoog 1962) or Lepoivre medium, may be used. Optionally, the pre-culture medium may comprise plant growth regulators, including auxin and cytokinin. In the present invention, plant explants were pre-cultured for four days in the dark on the Pre-Culture Medium of Table 2. Other pre-culture media and time periods of culture may be used.

TABLE 2

Plant Pre-Culture Medium

| Medium Components | Amount per Liter of Medium |
|---|---|
| WPM salts | 1 package (Sigma) |
| Ca(NO$_3$)$_2$•4H$_2$O | 3.7 g |
| MgSO$_4$•4H$_2$O | 0.37 g |
| Nicotinic Acid | 0.5 mg |
| Thiamine•HCl | 0.5 mg |
| Pyridoxin•HCl | 0.5 mg |
| D-Pantothenic Acid | 1.0 mg |
| Myo-inositol | 0.1 g |
| BA | 0.1-1 mg |
| Bacto-agar | 5-8 g |
| Acetosyringone | 5-200 mg |
| NAA | 0.2-3 mg |
| zeatin | 1-6 mg |

The methods of the present invention teach pre-culturing the explants on a pre-culture medium containing a high concentration of auxin or auxin-type growth regulators. Preferably, the auxin or an auxin-type growth regulator is selected from the group consisting of naphthaleneacetic acid (NAA), 2,4-Dichlorophenoxyacetic acid (2,4-D), indole-3-butyric acid (IBA), and indole-3-acetic acid (IAA). More preferably the auxin is NAA. The concentration range of said auxin is from about 0.1 to about 10 mg/l. The preferred auxin concentration is from about 0.2 to about 5 mg/l. More preferably, the auxin concentration is from about 0.2 to about 3 mg/l.

Preferably, the methods of the present invention provide for pre-culturing tree explants on a pre-culture medium comprising sufficient cytokinin. The cytokinin is selected from the group consisting of N$^6$-benzylaminopurine (BAP), N$^6$-benzyladenine (BA), zeatin, kinetin, 4-CPPU (N-(2-chloro-4-pyridyl)-N'-phenylurea)), thiadiazuron (TDZ), and 2-isopentenyladenine (2ip). The concentration range of said cytokinin is from about 0.25 to about 15 mg/l. Preferably, the cytokinin concentration range is from about 1 to about 10 mg/l. More preferably, the cytokinin concentration range is from about 1 to about 6 mg/l.

The methods of the present invention provide for pre-culturing tree explants on a pre-culture medium comprising an *Agrobacterium* inducer. The inducer may be acetosyringone. The concentration range of acetosyringone is from about 10 to about 400 mg/l. Preferably, the concentration range is from about 5 to about 200 mg/l.

The present invention contemplates the method of optionally pre-culturing tree explants on a pre-culture medium comprising both an auxin and an *Agrobacterium* inducer. The invention demonstrates that the combination of an auxin with an *Agrobacterium* inducer results in higher infection rates than either component independently. The explants can be pre-cultured on said pre-culture medium for about 1 to about 6 days prior to the introduction of *Agrobacterium*. Preferably, the explants are pre-cultured for about 4 days. The pre-culturing step can occur under both dark and light conditions; however, it is preferable to culture in the dark.

*Eucalyptus* explant transformation is performed with different strains of *A. tumefaciens* harboring a transformation vector. One such vector is GV2260, comprising a GUS gene operably linked to a promoter, such as an actin promoter or a constitutive promoter. The vector will also carry a herbicide resistance gene operably linked to a promoter. In the present invention, the acetolactate synthase (ALS) gene confers herbicide resistance and is driven by its *Arabidopsis* native promoter. See U.S. Pat. No. 6, 225,105. An *A. tumefaciens* culture suspended in induction medium (AIM formulation) is dripped by pipette on to the explants such that all cut edges are exposed to the bacteria. Alternatively, the explants may be transformed by vacuum infiltration, floral dip, and other methods of *Agrobacterium*-mediated transformation that are well known in the art. For a review of *Agrobacterium*-mediated transformation, see Gelvin, S B. *Microbiol. Mol Biol Rev* 67:1:16-37 (2003). Upon introduction of *Agrobacterium*, the explants are co-cultivated with the *Agrobacterium* for about 3 days on the same medium. Following co-cultivation, the explants are transferred to a shoot regeneration medium for the recovery of transgenic shoots.

The present invention teaches methods for shoot regeneration wherein transformed explants are cultured on a medium comprising a mixture of amino acids and vitamins, plant growth regulators, glucose, and an antioxidant. One such complete medium formulation is listed in Table 3 and is called Euc Regeneration medium. An antioxidant, such as ascorbic acid, may be added to the Euc Regeneration medium to minimize the exudation of plant phenolic compounds. Glucose and glutamine may be added to the medium to accelerate shoot regeneration. Antibiotics, such as carbenicillin, cefotaxime, and timentin can also be included in the medium to prevent bacterial overgrowth. Timentin is the preferred antibiotic. The antibiotic concentration ranges from about 75 to 800 mg/l. Preferably, the antibiotic concentration is about 400 mg/l.

The Euc Regeneration medium contains a mixture of amino acids that do not interfere with amino acid biosynthesis. In the present invention, the Euc Regeneration medium does not interfere with sulfonylurea-based herbicide selection. Preferably, the Euc Regeneration medium does not have branched chain amino acids (e.g. leucine, isoleucine, and valine). More preferably, the media has an amino acid mixture that replaces casein hydrolysate. Most preferably, the amino acid mixture has amino acids important for plant tissue culture growth.

TABLE 3

*Eucalyptus* Regeneration Medium

| Components for 1 Liter of Medium | Grams |
|---|---|
| KNO$_3$ | 1 |
| NH$_4$H$_2$PO$_4$ | 0.25 |
| MgSO$_4$•7H$_2$O | 0.25 |

TABLE 3-continued

Eucalyptus Regeneration Medium

| | Grams |
|---|---|
| CaCl$_2$•2H$_2$O | 0.10 |
| FeSO$_4$•7H$_2$O | 0.0139 |
| Na$_2$EDTA•2H$_2$O | 0.01865 |
| MES (Duchefa m1501) | 600.0 |
| MS Micro (½ strength) | |
| MnSO$_4$•H$_2$O | 0.00845 |
| ZnSO$_4$•7H$_2$O | 0.0043 |
| CuSO$_4$•5H$_2$O | 0.0000125 |
| CoCl$_2$•6H$_2$O | 0.0000125 |
| KI | 0.000415 |
| H$_3$BO$_3$ | 0.0031 |
| Na$_2$MoO$_4$•2H$_2$O | 0.000125 |
| Plant Growth Regulators | |
| Zeatin | |
| NAA (naphthalene acetic acid) | |
| Sugars | |
| Glucose/Sucrose | 20.0 |
| Myo-inositol | 0.100 |
| Amino acid and vitamine mix | |
| Nicotinic Acid | 0.010 |
| Thiamine | 0.010 |
| Ca Pantothenate | 0.001 |
| Pyridoxine | 0.001 |
| Biotin | 0.00001 |
| Ascorbic Acid | 0.050 |
| L-glutamine | 0.1 |
| Arginine | 0.0258 |
| Glycine | 0.00199 |
| Lysine | 0.0508 |
| Methionine | 0.0132 |
| Phenylalanine | 0.0257 |
| Serine | 0.00904 |
| Threonine | 0.00852 |
| Tryptophan | 0.0122 |
| Tyrosine | 0.0127 |
| Gelling Agent | |
| Gelrite | 3.0 |

In the present invention, there is a 4-day recovery period before the selection of transformed explants. To select for transformed explants, any selectable marker is added to the regeneration medium. Selectable markers include herbicides and antibiotics. Additionally, any screenable marker may be used to select a transformed plant. Examples of screenable markers include B-glucuronidase (GUS), green fluorescent protein (GFP), and luciferase. In the present invention, an herbicide selection agent is used. While the herbicide of the present invention is Alli, any herbicide may be used. Other herbicides include Oust and Liberty. The herbicide concentration may vary depending on the sensitivity of the explants from a specific species. The selected explants are subcultured every two to three weeks until the formation of adventitious buds. Transformed adventitious shoots are separated from shoot clumps and are stained for GUS (B-glucuronidase) expression. Jefferson et al. *EMBO:*6:13:901-3907 (1987). A reporter gene assay, such as GUS, is used to determine transformation efficiency and to ensure that the transformed shoots are not escapes or chimeras.

Upon confirmation of transformation via expression of a screenable marker gene, Southern blot analysis, PCR analysis, or other method known in the art, the transformed shoots are preferably transferred to a medium for shoot elongation. The present invention contemplates a shoot elongation medium comprising MS salts, sucrose, auxin, and giberellic acid. NAA is the preferred auxin and GA3 is the preferred giberellic acid. The shoots are cultured on the shoot elongation medium for about 10 to about 14 days, preferably under dark conditions. For the elongation of *E. dunii* clones, additional auxin needs to be added to the elongation media and the shoots should be cultured in the dark for the duration of the elongation.

Following shoot elongation, the shoots are excised and transferred to a root induction medium. Depending on the light conditions, it may be necessary to add plant growth regulators to the root induction medium. The methods of the present invention teach shoot excision at the node or immediately below the node. More preferably, the shoots are excised from a node near the shoot apex. One such rooting medium (Table 4) is comprised of BTM-1 nutrients (Chalupa 1988), activated carbon (MeadWestvaco, Nuchar), and an extra amount of CaCl$_2$. Alternatively, other low-salt media may be used for the root induction medium, such as Woody Plant Medium and ½ strength MS.

Depending on the light conditions, the rooting media may contain growth regulators to induce root formation. For example, under dark conditions that induce etiolation and auxin production in the shoot apical meristem, it may not be necessary to include auxin in the rooting medium. Additionally, if the shoots are excised in the dark, it may not be necessary to limit the origin of excision to the nodal regions and/or the shoot apex. Alternatively, if the rooting step occurs under light, it may be necessary to include auxin in the rooting medium. Furthermore, if the rooting step occurs in the light, it is preferable to excise the shoots at a node near the shoot apical meristem.

TABLE 4

Preferred rooting medium for *Eucalyptus*

| BTM-1 Media Components | mg/L |
|---|---|
| NH$_4$NO$_3$ | 412 |
| KNO$_3$ | 475 |
| Ca(NO$_3$)$_2$•4H$_2$O | 640 |
| CaCl$_2$•2H$_2$O | 440* |
| MgSO$_4$•7H$_2$O | 370 |
| KH$_2$PO$_4$ | 170 |
| MnSO$_4$•H$_2$O | 2.3 |
| ZnSO$_4$•7H$_2$O | 8.6 |
| CuSO$_4$•5H$_2$O | 0.25 |
| CoCl$_2$•6H$_2$O | 0.02 |
| KI | 0.15 |
| H$_3$BO$_3$ | 6.2 |
| Na$_2$MoO$_4$•2H$_2$O | 0.25 |
| FeSO$_4$•7H$_2$O | 27.8 |
| Na$_2$EDTA•2H$_2$O | 37.3 |
| Myo-inositol | 100 |
| Nicotinic acid | 0.5 |
| Pyridoxine HCl | 0.5 |
| Thiamine HCl | 1 |
| Glycine | 2 |
| Sucrose | 20000 |
| Activated Carbon | 5000 |

*Additional 400 mg/l CaCl$_2$•2H$_2$O is added to the medium

For species that are difficult to root, excised shoots can be pulse-treated with a medium having low levels of auxin to induce shoot formation. For example, a medium comprising 0.25 mg/l 2,4-D may be used for pulse treatment. Preferably, the shoots are pulse-treated for about 5-14 days before transferring to BTM-1 medium having activated carbon.

The transformation method of the present invention can be used for introducing any foreign DNA into a *Eucalyptus* or Pine species. Using the methods of the instant invention, any foreign DNA can be stably integrated into a plant cell and transmitted to progeny. For example, a gene involved in lignin biosynthesis, floral development, cellulose synthesis, nutrient uptake and transport, disease resistance, or enhanced resistance to an environmental condition can be introduced into a plant cell by the instant methods.

The methods of the present invention can be used for reducing gene expression in a *Eucalyptus* or pine species. Reduction of gene expression can be obtained by methods known in the art, including antisense suppression, co-suppression (sense suppression), and double stranded RNA interference. For a general review of gene suppression techniques, see *Science*, 288:1370-1372 (2000). Exemplary gene silencing methods are also provided in WO 99/49029 and WO 99/53050.

For antisense suppression, a cDNA sequence is arranged in a reverse orientation relative to the promoter sequence in a DNA construct. The cDNA sequence need not be full length relative to either the primary transcription product or fully processed mRNA. Generally, higher identity can be used to compensate for the use of a shorter sequence. Furthermore, the introduced sequence need not have the same intron or exon pattern, and identity of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 3500 nucleotides is especially preferred. The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other genes within a family of genes exhibiting identity or substantial identity to the target gene.

Another well known method of gene suppression in plants in sense co-suppression. Introduction of a nucleic acid sequence configure in the sense orientation provides an effective means by which to block the transcription of target genes. See, Assaad et al. *Plant Mol. Bio.* 22: 1067-1085 (1993); Flavell *Proc. Natl. Acad. Sci. USA* 91: 3490-3496 (1994); Stam et al. *Annals Bot.* 79: 3-12 (1997); Napoli et al., *The Plant Cell* 2:279-289 (1990); and U.S. Pat. Nos. 5,034,323, 5,231,020, and 5,283,184. For co-suppression, the introduced sequence need not be full length, relative to either the primary transcription product or fully processed mRNA. Preferably, the introduced sequence is not full length, so as to avoid a concurrent sense overexpression phenotype. In general, a higher identity in a shorter than full length sequence compensates for a longer, less identical sequence.

Using the methods of the instant invention, antisense suppression of a gene involved in lignin biosynthesis can be used to modify lignin content and/or composition in a transformed *Eucalyptus* plant. It has been demonstrated that antisense expression of sequences encoding cinnamyl alcohol dehydrogenase (CAD) in poplar, *N. tabacum*, and pine leads to the production of lignin having a modified monomeric composition. Grand et al., *Planta* 163: 232-37 (1985), Yahiaoui et al., *Phytochemistry* 49: 295-306 (1998), and Baucher et al., *Plant Physiol.* 112: 1479 (1996), respectively. Accordingly, the methods of the present invention can be used to stably transform and regenerate *Eucalyptus* species having antisense suppression of a foreign DNA involved in lignin biosynthesis.

The methods of the present invention can be used for regulating floral development in a *Eucalyptus* or pine species. Several gene products have been identified as critical components for anther development and pollen formation. For example, premature degradation of callose, which is essential for the formation of the microspore cell wall and microspore release, is sufficient to cause male sterility. Worrall et al., *Plant Cell* 4:7:759-71(1992). Accordingly, several methods have been developed for producing male sterile plants. U.S. Pat. No. 5,962,769, for example, describes transgenic plants rendered male sterile via expression of avidin. Avidin can be expressed constitutively, in a non-tissue specific manner, or in anther-specific tissues. In addition, male sterility can be induced by antisense suppression of chalcone synthase A gene. van der Meer et al., *The Plant Cell* 4:253 (1992). By the methods of the present invention, male sterile *Eucalyptus* and pine species can be produced and regenerated.

The present invention provides plant media comprising a sulfonylurea or related herbicide and a derivative of casein hydrolysate, wherein the derivative is substantially free of branched chain amino acids. Casein hydrolysate, also known as casein powder or casamino acids, is a mixture of amino acids and short peptide fragments obtained from the hydrolysis of casein. While various amino acid compositions are reported in the literature, and various amino acid compositions may be obtained from various sources of casein and various means of hydrolysis, casein hydrolysate obtained from any source by any means normally comprises branched chain amino acids including valine, leucine and isoleucine, aromatic amino acids such as tryptophan, and other amino acids such as glycine. Additionally, while the composition varies, practitioners agree that the compound is critical for initiating growth of plant cells, particularly many types of embryogenic cultures and conifer plant cells, in vitro. Supplementation of the inorganic media components with reduced nitrogen components such as amino acids, and in particular casein hydrolysate, is viewed by those skilled in the art of woody plant tissue culture, and particularly conifer tissue culture, as an essential component to induce or maintain the growth of cultures that can subsequently be regenerated into plants. For example, the initiation, induction and/or maintenance media of embryogenic cell culture of conifer species routinely comprise casein hydrolysate. See e.g. U.S. Pat. Nos. 5,034,326, 5,036,007, 5,041,382, 5,236,841, 5,310,672, 5,491,090, 5,413,930, 5,506,136, 5,534,433, 5,534,434, 5,563,061, 5,610,051, 5,821,126, 5,850,032, 6,200,809 and 6,518,485.

Thus, regardless of whether the media of subsequent culturing steps comprises casein hydrolysate, small amounts of the compound persist. Such trace amounts can wreak havoc during selection. For example, minute quantities of casein hydrolysate can inhibit the effectiveness of selection agents such as sulfonylureas, imidazolinones and triazolopyrimidines, which work to identify transgenic plant cells following transfection by a vector of interest.

As noted above, these selection agents target acetolactate synthase (ALS), which catalyzes the first common step in a plant's biosynthetic pathway of the branched-chain amino acids valine, leucine and isoleucine. Mutant forms of ALS which are resistant to these agents are utilized as selectable markers in recombinant DNA constructs and are paired with selection agents to identify transformed plant cells.

Therefore, minute quantities of casein hydrolysate in the selection medium enable untransformed cells to grow in the presence of sulfonylureas, imidazolinones or triazolopyrimidines. These false positives impede the production of transgenic plants since more samples have to be evaluated in order to identify desired transformants.

The present invention eliminates this problem by modifying the composition of casein hydrolysate so as to be substantially free of branched-chain amino acids. In another embodiment, the derivative of casein hydrolysate comprises a higher percentage of amino acids that are important in plant tissue culture growth, such as arginine or glutamine.

In another aspect, the invention provides a media composition for selecting transgenic plants comprising a tryptophan analog, wherein the media is substantially free of tryptophan.

Feedback-insensitive forms of the AS make useful selectable markers for plant transformations. These markers work in conjunction with tryptophan analogs to identify transformants. ASA2 is a preferred selectable marker.

Tryptophan appears routinely in plant media as a component of casein hydrolysate. The presence of minute concentrations of tryptophan in selection media can allow non-transformants to escape the selection process, thereby yielding false positives.

It was discovered that selecting transformants on media substantially free of tryptophan enhanced the selection process by reducing the number of false positives. Thus, one aspect of the present invention provides a method of selecting a transformed plant cell comprising transforming a plant cell with a vector comprising a gene of interest and a gene encoding a feedback-insensitive form of anthranilate synthase (AS), and growing the transformed cell on a media composition comprising a tryptophan analog, wherein the media is substantially free of tryptophan.

The methods, media and plasmids herein described are useful in selection of transgenic forest tree plants or lines using selection agents that alter amino acid metabolism, such as sulfonylurea and imidazolinone herbicides and methylated tryptophan analogs. They are further useful in selection, pre-selection and pre-transformation media used to culture plant material to be subjected to transformation with selectable markers that alter amino acid metabolism.

The methods, media and plasmids described above are further useful in the regeneration of plants from cell lines that have been selected using selection agents that alter amino acid metabolism. They can be for obtaining plants transformed with selectable markers that alter amino acid metabolism and that also may be resistant to herbicides that alter amino acid metabolism. Accordingly, the inventions herein also are useful for obtaining herbicide-resistant treestocks. In addition, the inventions are useful in providing crop material suitable for herbicide management of weeds in forestry plantings.

The inventive methods, media and plasmids can be used in the selection and regeneration of plants transformed with genes that result in overproduction of specific amino acids such as tryptophan. Accordingly, they may be further useful for obtaining treestocks showing increased or altered growth as a result of such overproduction.

The methods described herein are generally useful for developing and testing new selection media and selective agent doses. The same principles used to design these media can be applied to the design of selection media for positive selection methods, such as the use of normally non-metabolized sugars.

The inventive methods also are useful for developing formulations of amino acid mixtures to supplement plant tissue culture media.

Figure 2:
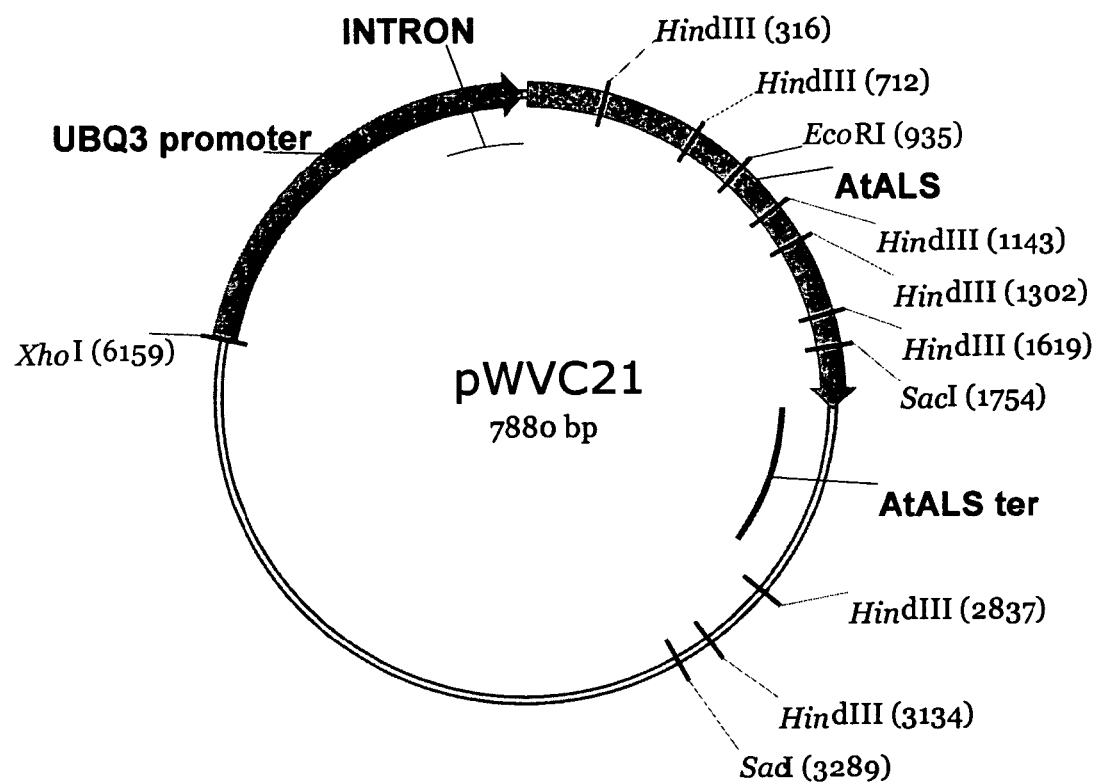
FIG. 2 provides a schematic representation of the vector pWVC21.
Figure 3:
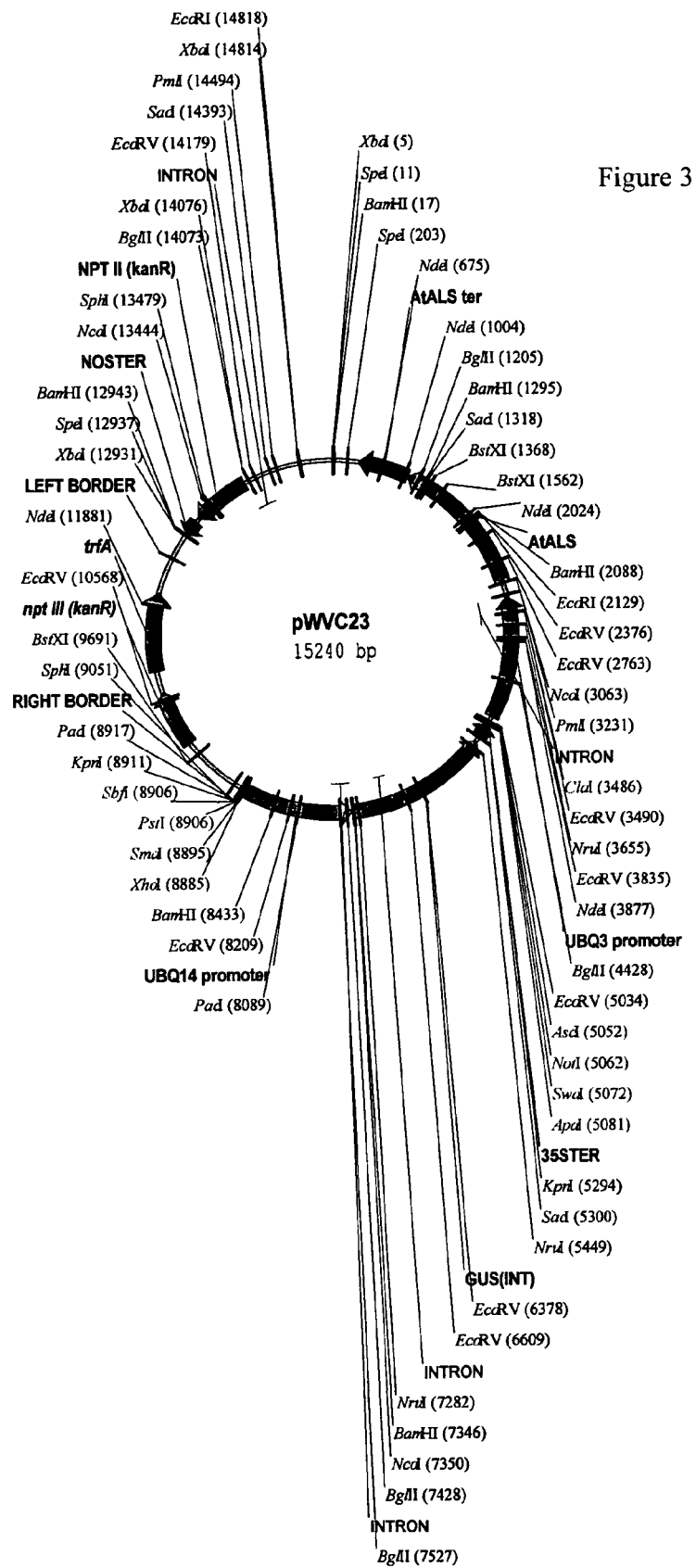
FIG. 3 provides a schematic representation of the vector pWVC23.
Figure 5A:
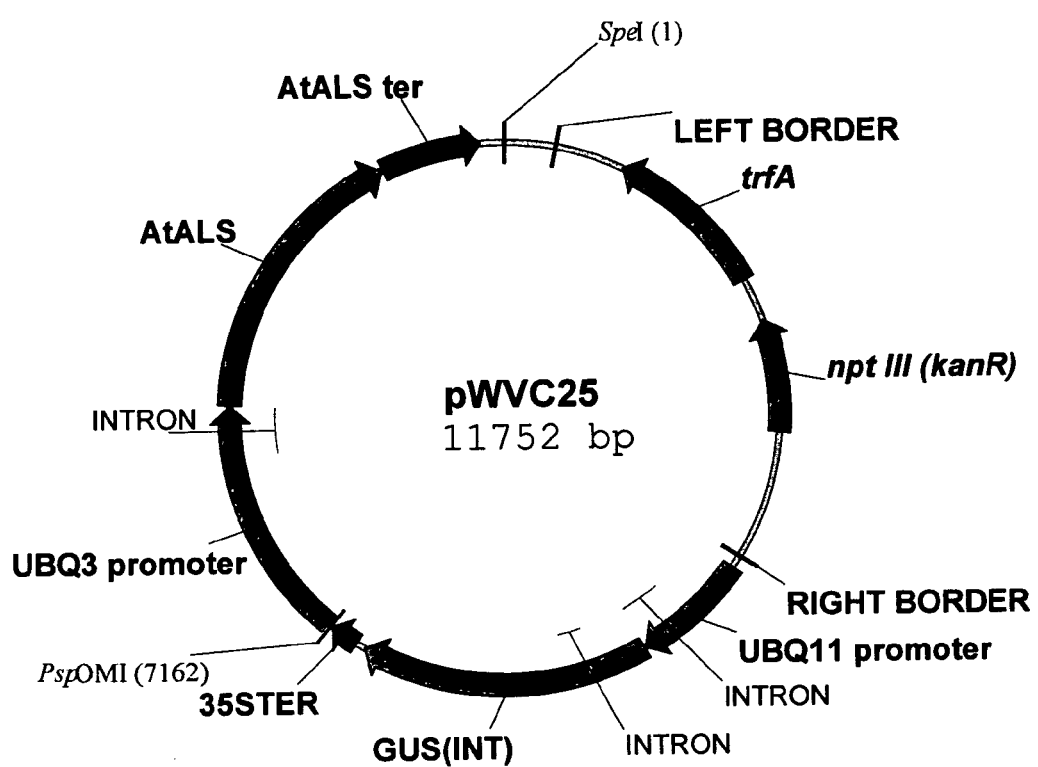
FIG. 5a provides a schematic representation of the vector pWVC25 and FIG. 5b provides a schematic representation of the vector pWVC26.
Figure 5B:
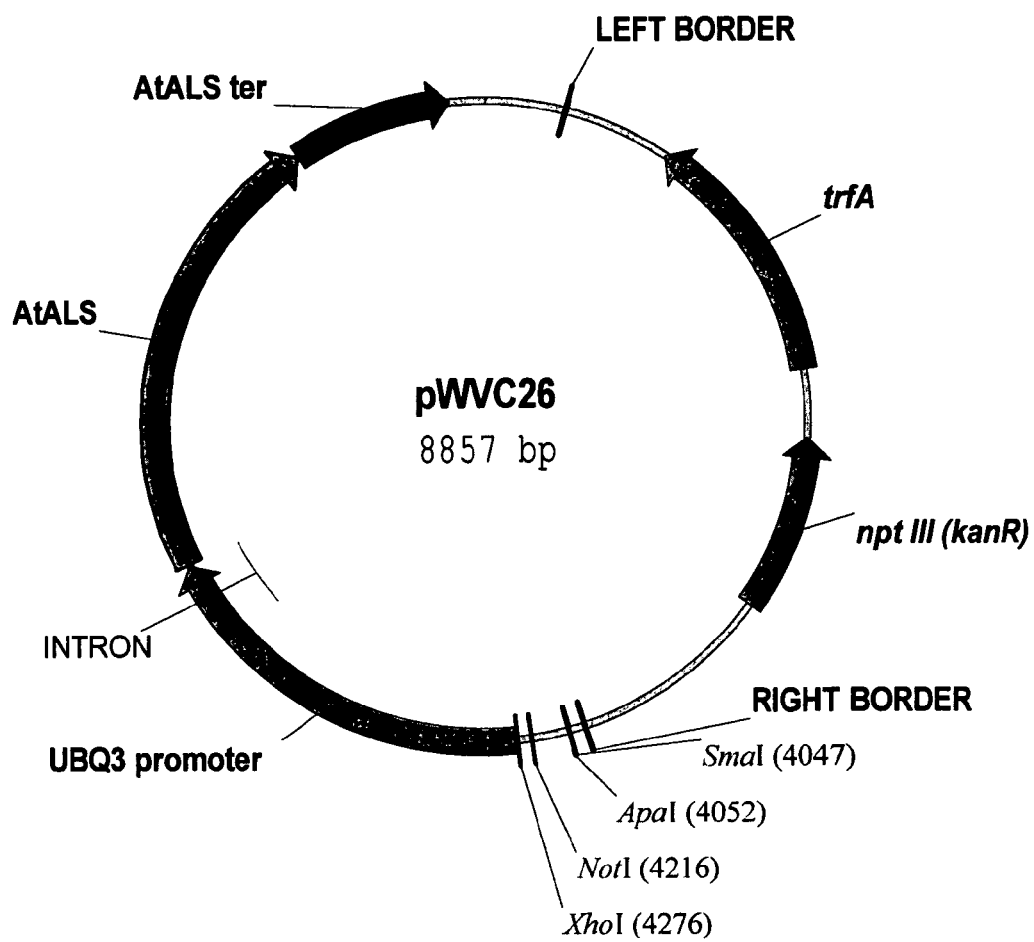
Figure 6:
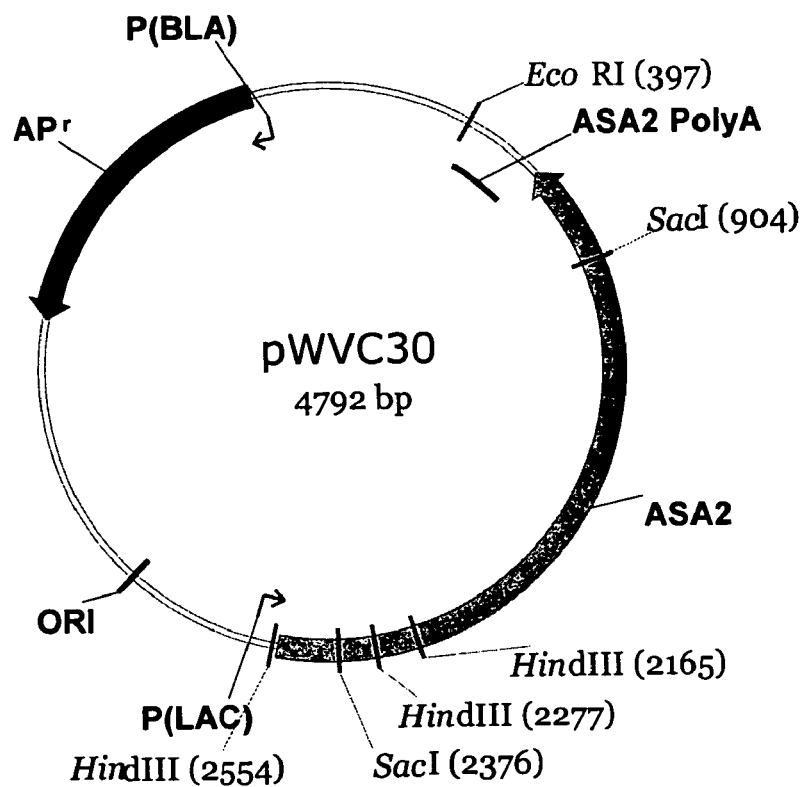
FIG. 6 provides a schematic representation of the vector pWVC30.

In another embodiment, the invention provides recombinant constructs useful for expressing heterologous protiens in plants. Examples of the invention vectors include the following:pWVC20 (FIG. 1), pWVC21 (FIG. 2), pWVC23 (FIG. 3), pWVC24 (FIG. 4), pWVC25 (FIG. 5a), pWVC26 (FIG. 5b), pWVC30 (FIG. 6), pWVC33 (FIG. 7), pWVC34 (FIG. 8a),and pWVC35 (FIG. 8b).

Another aspect of the invention provides methods of obtaining wood, wood pulp, paper, and oil from a plant transformed and selected by the methods of the present invention. Methods for transforming and selecting a transgenic plant are provided above and are known in the art. A transformed plant can be cultured or grown under any suitable conditions. For example, pine can be cultured and grown as described in U.S. Patent Application Publication No. 2002/0100083. *Eucalyptus* can be cultured and grown as in, for example, Rydelius, et al., Growing Eucalyptus for Pulp and Energy, presented at the Mechanization in Short Rotation, Intensive Culture Forestry Conference, Mobile, Ala., 1994. Wood, wood pulp, paper, and oil can be obtained from the plant by any means known in the art.

As noted above, the wood and wood pulp obtained in accordance with this invention may demonstrate improved characteristics including, but not limited to any one or more of lignin composition, lignin structure, wood composition, cellulose polymerization, fiber dimensions, ratio of fibers to other plant components, plant cell division, plant cell development, number of cells per unit area, cell size, cell shape, cell wall composition, rate of wood formation, aesthetic appearance of wood, formation of stem defects, rate of growth, rate of root formation ratio of root to branch vegetative development, leaf area index, and leaf shape include increased or decreased lignin content, increased accessibility of lignin to chemical treatments, improved reactivity of lignin, increased or decreased cellulose content increased dimensional stability, increased tensile strength, increased shear strength, increased compression strength, increased shock resistance, increased stiffness, increased or decreased hardness, decreased spirality, decreased shrinkage, and differences in weight, density, and specific gravity.

Phenotype can be assessed by any suitable means. The plants can be evaluated based on their general morphology. Transgenic plants can be observed with the naked eye, can be weighed and their height measured. The plant can be examined by isolating individual layers of plant tissue, namely phloem and cambium, which is further sectioned into meristematic cells, early expansion, late expansion, secondary wall formation, and late cell maturation. See, e.g., Hertzberg, supra. The plants also can be assessed using microscopic analysis or chemical analysis.

Microscopic analysis includes examining cell types, stage of development, and stain uptake by tissues and cells. Fiber morphology, such as fiber wall thickness and microfibril angle of wood pulp fibers can be observed using, for example, microscopic transmission ellipsometry. See Ye and Sundström, *Tappi J.*, 80:181 (1997). Wood strength, density, and grain slope in wet wood and standing trees can be determined by measuring the visible and near infrared spectral data in conjunction with multivariate analysis. See, U.S. Patent Application Publication Nos. 2002/0107644 and 2002/0113212. Lumen size can be measured using scanning electron microscopy. Lignin structure and chemical properties can be observed using nuclear magnetic resonance spectroscopy as described in Marita et al., *J. Chem. Soc., Perkin Trans.* 12939 (2001).

The biochemical characteristic of lignin, cellulose, carbohydrates and other plant extracts can be evaluated by any standard analytical method known including spectrophotometry, fluorescence spectroscopy, HPLC, mass spectroscopy, and tissue staining methods.

It will be readily apparent to one of ordinary skill in the relevant arts that other suitable modifications and adaptations to the methods and applications described herein can be made without departing from the scope of the invention or any embodiment thereof.

The following examples are set forth as representative of specific and preferred embodiments of the present invention. These examples are not to be construed as limiting the scope of the invention in any manner. It should be understood that many variations and modifications can be made while remaining within the spirit and scope of the invention.

EXAMPLES

Example 1

Plant Materials

All elite clones were maintained as shoot clumps in Magenta boxes and subcultured every 4-6 weeks. Shoot clumps were divided as needed and maintained as stock culture. Unless noted otherwise, all cultures were grown under shaded, cool fluorescent light with a light intensity of 30-40 µE/m$^2$/s with a photoperiod of 16 hours, and the temperature of the growth room is 21° C. Except for the selected *E. dunnii* clones, leaf explants were used for all selected clones.

Commercial *E. dunnii* elite clone DUN00001 were provided by Rijesa, a subsidiary of MeadWestvaco Brazil. Shoot clumps were maintained at 4 clumps per Magenta box. The preferred explant for these clones are tissues with advanced vascular tissues, such as internodes, petioles and midribs.

*E. grandis* clones were provided by Rubicon, New Zealand. *E. grandis* clones were received as shoot clumps on solid medium. The clumps were transferred to Euc Maintenance medium (Table 1) with BA at 0.25-0.5 mg/l in Magenta boxes. The shoot clumps were transferred to fresh medium every 4-6 weeks.

Commercial *E. grandis×urophylla* clones IPB1 were provided by International Paper, USA. Shoot clumps were received the same way as described for *E. grandis*. The stock establishment procedures and the culture conditions were the same as with *E. grandis*, except that all cultures were grown under full light conditions at an intensity of about 120 µE/m$^2$/s.

Commercial *E. camaldulensis* clones were received as cuttings from International Paper, USA. Newly flushed apical and axillary shoots were surface sterilized with 10-15% commercial bleach for 5-10 minutes, a quick rinse with 70% ethanol, and three rinses with sterile water. Nodes were separated and cultured on Euc Maintenance medium. When axillary shoots initiate from the nodes, they were transferred to fresh Euc maintenance medium for further proliferation. Stock cultures were established on the same medium after 3-4 culture cycles. The stock cultures were maintained under the same condition as previously described for the other clones.

Example 2

Construct

Two constructs were used for the transformation experiments: pWVZ20 and pWVR133. Binary plasmid pWVZ20 contains an herbicide resistant gene driven by a plant promoter and the β-glucuronidase (GUS) gene driven by a constitutive promoter between T-DNA borders. Binary plasmid pWVR133 contains the same herbicide resistant gene construct, but the GUS gene contains an intron and is driven by an actin promoter. GUS expression of pWVR133 only occurs in plant cells but not in bacterial cells. The *Agrobacterium* strain GV2260 (Deblaere et al. 1985) was used for the transformation studies. One of ordinary skill in the art would be able to use any binary construct having an herbicide resistant gene operably linked to a constitutive plant promoter.

Example 3

Preparation of *Agrobacterium* for Transformation

*Agrobacterium* containing either pWVZ20 or pWVR133 were grown on YEP medium (10 g/l yeast extract, 10 g/l peptone and 50 mg/l NaCl, pH 7.0-7.2) for 3 days. A single colony from the plate was selected and grown in 20-50 ml liquid YEP medium with kanamycin at 100 mg/l and rifampicin 50 mg/l. Cultures were incubated overnight in a shaking incubator at 28° C. and 150 rpm. The over night culture with an OD of about 0.6-1.1 was spun down in a desktop centrifuge at 3000 g for 20 minutes and resuspended with *Agrobacterium* Induction Medium or AIM (WPM salts with glucose at 5 g/l, 250 µM acetosyringone, 2 mM phosphate buffer, and 0.05 M MES, pH 5.8) with an OD of about 0.6-1.1. Cultures were incubated for 25 minutes at 28° C. before infection. Bacterial concentration was determined before and after infection.

Example 4

Preparation of Explants for Infection and Pre-Culture

*Eucalyptus* stock cultures maintained on Euc Maintenance medium were used as the sources of the explants. Although leaves, petioles, internodes, floral tissues, and embryogenic tissues can be used for transformation, leaf explants were selected because leaves are abundant. Healthy and newly opened leaves were selected for transformation. The tip portions of the leaves were removed by scissors or forceps to increase the number of wounded cells. Explants were placed on pre-culture medium (Table 2) abaxial side down. The pre-culture medium is a nutrient medium upon which plant explants are cultured before *Agrobacterium* transformation. Specifically, the inventive pre-culture medium increases transformation efficiency and plant regeneration. While the present pre-culture medium comprises acetosyringone, other *Agrobacterium* inducers may be used. Woody Plant Medium (WPM) salts (Loyd and McCown, 1980) were used in the present pre-culture medium; however, other salt media, such as MS medium (Murashige and Skoog 1962) or Lepoivre medium, may be used. Optionally, the pre-culture medium may comprise plant growth regulators, including auxin and cytokinin.

In the present invention, plant explants were pre-cultured for four days in the dark on the pre-culture medium displayed in Table 2. While not required, the instant pre-culture medium contained both auxin and cytokinin. Additionally, plant explants may be cultured on the pre-culture medium from one to six days before *Agrobacterium* transformation.

Example 5

*Agrobacterium* Inoculation and Removal

Induced *Agrobacterium* culture was prepared as described in Example 3 and the culture was dripped onto each explant by pipette. Sufficient *Agrobacterium* culture was dripped to ensure that all the cut edges were covered with bacterial solution. Alternatively, the explants may be transformed by vacuum infiltration, floral dip, and other methods of *Agrobac-*

*terium*-mediated transformation. Following transformation, explants covered with *Agrobacterium* culture were placed in the dark for four days of co-cultivation. Alternatively, the explants may be co-cultivated with *Agrobacterium* under light conditions. Additionally, the explants may be co-cultivated with *Agrobacterium* under light or dark conditions for 2-10 days, preferably 4 days. Following co-cultivation, the explants were transferred to Euc Regeneration medium (Table 3) with 400 mg/l timentin. There is no need to wash explants. Explants were cultured on this medium for four days before transfer to a selection medium. In the present example, the selection medium is the Euc Regeneration medium supplemented with both timentin and an herbicide selection agent.

Example 6

Regeneration of Transgenic Shoots

Shoot clumps that survive selection are maintained on Euc regeneration medium containing herbicide and timentin, and they are transferred every 3 weeks until shoots proliferate and initially elongate. For transformation experiments with pWVR133, leaf and stem tissues from the regenerated shoots are stained for GUS expression as soon as the shoots are developed. For transformation experiments with pWVZ20, leaf and stem tissues from the regenerated shoots are stained for GUS expression when the shoots are further developed and free from residual *Agrobacterium*.

Example 7

GUS Staining

GUS staining was performed to monitor the frequency of *Agrobacterium* infection and to ensure that the selected shoots are not escapes or chimeras. For transformation experiments with pWVR133, the leaf and stem tissues from the regenerated shoots were stained for GUS expression immediately upon shoot development. For transformation experiments with pWVZ20, leaf and stem tissues from the regenerated shoots were stained for GUS expression when shoots are further developed and free from residual *Agrobacterium*. To determine GUS activity, the explants were incubated in a substrate comprising 100 mM phosphate buffer (pH 7.0), 0.05% dimethyl suphoxide, 0.05% Triton X-100, 10 mM EDTA, 0.5 mM potassium ferrocyanide, and 1.5 mg/ml 5-bromo-4-chloro-3-indolyl-β-D-glucuronide (X-gluc). The explants were subjected to 10 minutes of vacuum before an overnight incubation at 37° C. Following overnight incubation, GUS foci were counted.

Example 8

RNA Isolation

RNA was isolated from leaf and shoot tissues of wild-type and transformed *E. grandis, E. grandis×urophylla*, and *E. camadulensis* plants with RNAqueous™-96 kit, according to the manufacturer's instructions. Briefly, 0.1 to 1.5 mg tissue was suspended in 300 µl Lysis/Binding buffer and ground to a fine powder with a plastic pestle. The samples were centrifuged at maximum speed for 3 minutes and the supernatant was transferred to a fresh plate. Three hundred µl (1× v/v) 64% ethanol was added to the supernatant and the samples were vortexed briefly. The samples were then centrifuged for 2 minutes at 1850 g. Following centrifugation, an optional DNase treatment step was performed. To each sample, 5 µl DNase+35 µl DNase buffer was added to the center of the filter pad and the samples were incubated at room temperature for 20 minutes. After the 20 minute incubation, 600 ml Wash Buffer A was added to each sample and the samples were centrifuged at maximum speed for 2 minutes. Following centrifugation, the supernatants were discarded and 600 µl Wash Buffer B was added to the filter pad of each sample. Following centrifugation at maximum speed for 2 minutes, the supernatants were discarded and 600 µl Wash Buffer C/D was added to each filter pad. The samples were centrifuged at maximum speed for 2 minutes and the supernatants were discarded. Following a second rinse with Wash Buffer C/D, 50 µl RNA elution solution was added and the samples were centrifuged at maximum speed for 2-3 minutes. The RNA elution step was repeated and the eluted RNA samples were stored at −80 degrees Celsius until further use.

Example 9

RT-PCR

To determine the presence and expression of the ALS herbicide resistance gene, RT-PCR was performed. Total RNA was isolated, as described in Example 8, from transformed and wild-type samples of *E. grandis, E. grandis×urophylla*, and *E. camadulensis* plants. Following RNA isolation and quantitation, RT-PCR was performed with Ready to Go RT-PCR kit (Pharmacia), according to the manufacturer's instructions. Generally, 5 µl total RNA (about 20 ng RNA) was added to a 45 µl RT-PCR reaction mixture containing 1 µl Oligo dTn, 1 µl 3 µM ALS forward primer, 1 µl 3 µM ALS reverse primer, and 42 µl water.

To denature the RNA, the tubes were heated to a temperature of at least 75° C. for 3 minutes. The samples were then incubated at 42° C. for 30 minutes. Following incubation, RT-PCR was performed as follows:

Cycle 1:
95° C. for 5 minutes
55° C. for 1 minute
72° C. for 1 minute
Cycles 2-30
95° C. for 1 minute
55° C. for 1 minute
72° C. for 1 minute
Cycle 31
95° C. for 1 minute
55° C. for 1 minute
72° C. for 10 minutes Following completion of RT-PCR, the PCR amplification products were visualized on an agarose gel stained with ethidium bromide.

Example 10

Optimization of Growth Regulators

This example teaches a method to optimize the levels of growth regulators for shoot regeneration from the recalcitrant commercial *E. dunnii* clone DUN00001 or other recalcitrant clones. Internodal explants are prepared as described in Example 1 and are inocultated with *Agrobacterium* as described in Example 5. Following co-cultivation, transformed shoot clumps are transferred to a shoot regeneration medium. In studies prior to this example, only the combination of zeatin and NAA gave rise to shoot regeneration, and other combinations from cytokinins BA, 2ip and auxin 2,4-D, IAA, IBA did not produce adventitious shoots. To optimize the auxin and cytokinin concentrations in the shoot regeneration media, several combinations of hormones were evaluated as a function of the production of elongated shoots. Many combinations such as the TDZ and NAA produce shoot primordia but not elongated shoots. During the initial screening, the zeatin levels were 10, 1, and 0.1 mg/l and the NAA levels were 0.01, 0.1 and 1 mg/l. Zeatin had better results at 10 mg/l than at 1 mg/l or 0.1 mg/l. The following data summarize the attempt to optimize the level of zeatin and NAA.

TABLE 5

Effect of zeatin and NAA levels on the production of green shoot primordia (GSP) and elongated shoots.

| Zeatin/NAA (mg/l) | Total Explant Pieces | GSP Frequency (%) | Regeneration Frequency (%) |
|---|---|---|---|
| (a) | | | |
| 5/0.01 | 18 | 61 | 0 |
| 5/0.03 | 18 | 39 | 0 |
| 5/0.05 | 18 | 56 | 0 |
| 5/0.07 | 18 | 33 | 17 |
| 5/0.09 | 18 | 33 | 6 |
| 5/0.11 | 18 | 44 | 44 |
| 10/0.01 | 18 | 67 | 6 |
| 10/0.03 | 18 | 50 | 0 |
| 10/0.05 | 18 | 72 | 0 |
| 10/0.07 | 18 | 61 | 0 |
| 10/0.09 | 18 | 50 | 0 |
| 10/0.11 | 18 | 56 | 0 |
| (b) | | | |
| 5/0.01 | 90 | 47 | 1 |
| 5/0.03 | 90 | 51 | 7 |
| 5/0.05 | 90 | 34 | 4 |
| 5/0.07 | 90 | 38 | 3 |
| 5/0.09 | 90 | 53 | 13 |
| 5/0.11 | 90 | 62 | 24 |
| 10/0.01 | 90 | 31 | 2 |
| 10/0.03 | 90 | 56 | 3 |
| 10/0.05 | 90 | 52 | 4 |
| 10/0.07 | 90 | 56 | 4 |
| 10/0.09 | 90 | 66 | 2 |
| 10/0.11 | 90 | 64 | 8 |

Two experiments consistently showed that zeatin at 5 mg/l is better than 10 mg/l, and NAA at 0.11 mg/l is better than the low levels for shoot induction. Further studies showed that lower levels of zeatin is not as effective as 5 mg/l for regeneration of recalcitrant clones such as the selected *E. dunnii* clones, and increases in NAA tend to induce undesired callus growth. Thus, zeatin at 5 mg/l and NAA at 0.11 mg/l is selected as the basic growth regulators for the Euc Regeneration medium.

The Euc Regeneration medium can be used for inducing shoot development for any clone. As different clones may need different concentrations of plant growth regulators, the Euc Regeneration Medium should be optimized for each clone. The Euc Regeneration medium is routinely used to induce adventitious shoots for selected clones like *E. grandis* clones FC1-5, FC9, *E. camaldulensis* clone 4590, and *E. grandis×urophylla* clone IPB1. The regeneration efficiency is usually greater than 90 percent after 12 weeks of culture.

Example 11

Amino Acid Mix for Shoot Regeneration

This example teaches the use of the amino acid and vitamin mix (see formula in Table 2) to accelerate the shoot regeneration process by promoting the growth of shoot masses. Leaf explants of *E. grandis* clone FC3 were prepared as described in Example 1 and *Agrobacterium* inoculum is prepared according to Example 4. Leaf explants were inoculated as described in Example 5 and co-cultivated for three days. Following co-cultivation, leaf explants were harvested and placed on medium with or without the amino acid mix at 10 pieces per Magenta box. At 4 weeks, the early phase of organogenesis was evaluated as the frequency of explants forming adventitious shoots and the size of the clumps with shoot primordia, small shoots and callus was measured (See Table 6).

TABLE 6

Effect of the amino acid mix on shoot organogenesis of *E. grandis* clone FC3.

| Euc Regeneration Medium | Number of Explants | Percent of Explants with Shoot Primordia | Mean Clump Size (cm$^2$) ± Standard Errors |
|---|---|---|---|
| With Amino Acid Mix | 30 | 100 | 1.39 ± 0.09 |
| Without Amino Acid Mix | 30 | 100 | 0.98 ± 0.09 |

As shown in this study, the inclusion of the amino acid mix (Table 2) accelerated shoot regeneration through an increase in clump size.

Example 12

Method for Increasing Infection Rate

This example teaches a method for increasing *Agrobacterium* infection rate. In particular, this example teaches a method that stimulates cell growth, increases the number of target cells, and promotes infection. Explants from elite *Eucalyptus grandis×urophylla* Clone IPB1 were prepared as described in Example 1 and *Agrobacterium* strain GV2260 containing pWVR133 was prepared as described in Example 3. Harvested explants were incubated in the dark for 4 days either on *Eucalyptus* regeneration medium or a medium with various auxin-rich growth regulators. *Agrobacterium* culture was dripped on explants and co-cultured with the explants on the same medium for 3 days in dark. Then, explants were removed from the *Agrobacterium* puddle and transferred to Euc Regeneration medium supplemented with 400 mg/l timentin for 4 days. Following transfer to regeneration medium, the explants were stained for GUS expression. As shown in Tables 7-8, various auxin-type growth regulators had a positive effect on GUS expression 7 days post infection.

TABLE 7

Auxin Pre-treatment Increases the *Agrobacterium* Infection Rate for an Elite *Eucalyptus grandis* x *urophylla* Clone IPB1

| Pre-treatment Medium (EucReg Medium + PGR in mg/l) | No. Explants | No. GUS+ | % GUS+ | No. GUS Foci | Avg. No. Foci/ Responding Explant |
|---|---|---|---|---|---|
| 5.0 zeatin/0.1 NAA (Control Regeneration Medium) | 25 | 3 | 12 | 6 | 2.3 |
| 0.25 2,4-D/0.5 zeatin | 24 | 4 | 17 | 7 | 1.5 |
| 1.0 2,4-D/0.5 zeatin | 25 | 15 | 60 | 155 | 10.3 |

Although there is a significant increase in infection rate and the number of cells expressing GUS, the control shows a delay of shoot regeneration from medium with 1.0 mg/l 2,4-D. The zeatin level is raised to 5 mg/l, the same level as the level in regeneration medium

TABLE 8

Various Auxin-type Growth Regulators Show Positive Influence on Infection of an Elite *Eucalyptus grandis* x *urophylla* Clone IPB1

| Pre-treatment Medium (EucReg Medium + 5 mg/l zeatin + auxins in mg/l) | No. Explants | No. GUS+ | % GUS+ | No. GUS Foci | Avg. No. Foci/ Responding Explant |
|---|---|---|---|---|---|
| 0.1 NAA (Control Regeneration Medium) | 25 | 4 | 16 | 5 | 1.3 |
| 1.0 2,4-D | 25 | 12 | 48 | 64 | 5.3 |
| 0.5 2,4-D | 25 | 20 | 80 | 97 | 4.9 |
| 2.0 NAA | 25 | 9 | 36 | 30 | 3.3 |
| 1.0 NAA | 25 | 13 | 52 | 35 | 2.7 |
| 3.0 IAA | 48 | 46 | 96 | 565 | 12.3 |
| 2.0 IAA | 25 | 16 | 64 | 167 | 10.4 |
| 1.0 IAA | 25 | 16 | 64 | 116 | 7.3 |
| 1.0 TDZ | 25 | 0 | 0 | 0 | 0.0 |
| 0.5 TDZ | 25 | 1 | 4 | 3 | 3.0 |
| 0.1 TDZ | 25 | 3 | 12 | 25 | 8.3 |

The results from experiments above show that pre-culture of explants with medium rich in various auxin-type plant growth regulators increases the infection rate as evaluated by the frequency of explants with GUS foci and the average number of GUS foci per responding explant. In addition, the regeneration is not affected by the pre-culture in control experiments.

Example 13

*Agrobacterium* Inducer Improves Infection Rate

This example shows that the inclusion of acetosyringone (AS) alone in the pre-culture medium improves the infection rate significantly. In this experiment, leaf explants from *E. grandis* clones FC3 and FC5 were pre-cultured for four days with four media: Euc Regeneration medium, Euc Regeneration medium with 250 µM or 750 µM acetosyringone, or Euc Regeneration medium with the growth regulator combination 0.25 mg/l 2,4-D and 5 mg/l zeatin. Then explants were infected with *Agrobacterium* and co-cultivated for three days on the same medium before transfer to Euc Regeneration medium with 400 mg/l timentin. GUS staining was performed four days after co-cultivation. The data is summarized in Tables 9-10.

TABLE 9

Effect of acetosyringone on *Agrobacterium* infection of *E. grandis* clones FC3

| Pre-culture Medium (EucReg Medium + PGR in mg/l) | No. Explants | No. GUS+ | % GUS+ | No. GUS Foci | Avg. No. Foci/ Responding Explant |
|---|---|---|---|---|---|
| 5.0 zeatin/ 0.1 NAA (Control Regeneration Medium) | 25 | 2 | 8 | 4 | 2 |
| 5.0 zeatin/ 0.1 NAA + 250 µM AS | 25 | 19 | 76 | 162 | 8.5 |
| 5.0 zeatin/ 0.1 NAA + 750 µM AS | 25 | 22 | 88 | 232 | 10.5 |
| 5.0 zeatin/0.25 2,4-D | 25 | 16 | 64 | 62 | 3.9 |

TABLE 10

Effect of acetosyringone on *Agrobacterium* infection of *E. grandis* clones FC5

| Pre-culture Medium (EucReg Medium + PGR in mg/l) | No. Explants | No. GUS+ | % GUS+ | No. GUS Foci | Avg. No. Foci/ Responding Explant |
|---|---|---|---|---|---|
| 5.0 zeatin/ 0.1 NAA (Control Regeneration Medium) | 25 | 0 | 0 | 0 | 0 |
| 5.0 zeatin/ 0.1 NAA + 250 µM AS | 25 | 3 | 12 | 4 | 1.3 |
| 5.0 zeatin/ 0.1 NAA + 750 µM AS | 26 | 9 | 35 | 23 | 2.6 |
| 5.0 zeatin/0.25 2,4-D | 26 | 14 | 54 | 51 | 3.6 |

The results indicate that AS alone in the pre-culture medium stimulates infection. In addition, GUS staining indicates that AS increases the infection of the wounded cells along the cut edges, where transgenic plants normally arise.

Example 14

Combining *Agrobacterium* Inducer and Growth Regulator Improves Infection Rate

This example indicates that the combination of AS and auxins in the pre-culture phase could increase the infection rate even higher. In the following examples, explants from *E. grandis* clones FC1-5 and *E. grandis*×*urophylla* clone IPB1 were cultured on auxin-rich pre-culture medium with or without 250 µM AS before infection. Explants were pre-cultured with Euc Regeneration medium as the control. Following pre-culture, the explants were inoculated with *Agrobacterium* as described in Example 5.

TABLE 11

Effect of combining auxin with *Agrobacterium* inducer on infection

| Pre-culture Medium (EucReg Medium + PGR in mg/l) | No. Explants | No. GUS+ | % GUS+ | No. GUS Foci | Avg. No. Foci/ Responding Explant |
|---|---|---|---|---|---|
| (a) *E. grandis* x *urophylla* clone IPB1 | | | | | |
| 5.0 zeatin/0.1 NAA (Control Regeneration Medium | 50 | 11 | 22 | 37 | 3.4 |
| 5.0 zeatin/0.25 2,4-D | 50 | 36 | 72 | 388 | 10.8 |
| 5.0 zeatin/0.25 2,4-D + AS | 50 | 42 | 84 | 754 | 18.0 |
| 5.0 zeatin/2 IAA | 49 | 36 | 73 | 289 | 8.0 |
| 5.0 zeatin/2 IAA + AS | 49 | 47 | 96 | 855 | 18.2 |
| (b) *E. grandis* clone FC1 | | | | | |
| 5.0 zeatin/0.1 NAA (Control Regeneration Medium | 25 | 7 | 28 | 17 | 2.4 |
| 5.0 zeatin/0.25 2,4-D | 25 | 11 | 44 | 65 | 5.9 |
| 5.0 zeatin/0.25 2,4-D + AS | 25 | 17 | 68 | 106 | 6.2 |
| 5.0 zeatin/2 IAA | 24 | 15 | 63 | 76 | 5.1 |
| 5.0 zeatin/2 IAA + AS | 25 | 24 | 96 | 272 | 11.3 |
| (c) *E. grandis* clone FC3 | | | | | |
| 5.0 zeatin/0.1 NAA (Control Regeneration Medium | 25 | 0 | 0 | 0 | 0 |
| 5.0 zeatin/0.25 2,4-D | 25 | 17 | 68 | 97 | 5.7 |
| 5.0 zeatin/0.25 2,4-D + AS | 25 | 17 | 68 | 77 | 4.5 |
| 5.0 zeatin/2 IAA | 24 | 7 | 28 | 11 | 1.6 |
| 5.0 zeatin/2 IAA + AS | 25 | 14 | 56 | 66 | 4.7 |
| (d) *E. grandis* clone FC4 | | | | | |
| 5.0 zeatin/0.1 NAA (Control Regeneration Medium | 51 | 7 | 14 | 33 | 4.7 |
| 5.0 zeatin/0.25 2,4-D | 50 | 13 | 26 | 26 | 2.0 |
| 5.0 zeatin/0.25 2,4-D + AS | 50 | 22 | 44 | 111 | 5.0 |
| 5.0 zeatin/2 IAA | 51 | 6 | 12 | 23 | 3.8 |
| 5.0 zeatin/2 IAA + AS | 50 | 24 | 48 | 173 | 7.2 |
| (e) *E. grandis* clone FC5 | | | | | |
| 5.0 zeatin/0.1 NAA (Control Regeneration Medium | 26 | 4 | 15 | 10 | 2.5 |
| 5.0 zeatin/0.25 2,4-D | 25 | 17 | 68 | 113 | 6.6 |
| 5.0 zeatin/0.25 2,4-D + AS | 26 | 21 | 81 | 135 | 6.4 |
| 5.0 zeatin/2 IAA | 25 | 9 | 36 | 30 | 3.3 |
| 5.0 zeatin/2 IAA + AS | 26 | 21 | 81 | 100 | 4.8 |
| (f) *E. grandis* x *saligna* clone FC12 | | | | | |
| 5.0 zeatin/0.25 2,4-D | 25.0 | 14.0 | 56.0 | 86.0 | 6.1 |
| 5.0 zeatin/0.25 2,4-D + AS | 25.0 | 21.0 | 84.0 | 297.0 | 14.1 |
| 5.0 zeatin/2 IAA | 25.0 | 18.0 | 72.0 | 195.0 | 10.8 |
| 5.0 zeatin/2 IAA + AS | 25.0 | 23.0 | 92.0 | 363.0 | 15.8 |

These results show a consistent beneficial effect on infection across a range of clones by using both AS and auxin stimulation in the pre-culture medium. The clones have an increase in both the infection frequency and the average number of GUS foci per responding explant. In addition, the infection of wounded cells along the cutting edge significantly increases.

Example 15

This example shows that the combination of AS and auxins in the co-cultivation phase further increases the infection rate. Leaf explants from commercial *E. dunnii* clone DUN00003 were pre-cultured on regeneration medium containing either 750 µM AS alone or the combination of 250 µM AS and an elevated auxin concentration (2 mg/l IAA vs. 0.1 mg/l NAA). Explants were infected with *Agrobacterium* strain GV2260 containing pWVR31, containing a GUS gene (driven by a constitutive promoter) and an NPTII gene (driven by a different constitutive promoter). In this example, the explants are inoculated with *Agrobacterium* directly (without pre-culture) and are assayed for GUS expression after 4 days of co-cultivation.

TABLE 12

*E. dunnii* clone DUN00003 leaf explants

| Pre-culture Medium (EucReg Medium + PGR in mg/l) | No. Explants | No. GUS+ | % GUS+ | No. GUS Foci | Avg. No. Foci/ Responding Explant |
|---|---|---|---|---|---|
| 5.0 zeatin/ 0.1 NAA + 750 µM AS | 23 | 8 | 35 | 15 | 1.9 |
| 5.0 zeatin/ 2 IAA + 250 µM AS (rep1) | 23 | 13 | 57 | 103 | 7.9 |
| 5.0 zeatin/ 2 IAA + 250 µM AS (rep 2) | 23 | 13 | 57 | 35 | 2.7 |

Example 16

This example shows that the combination of AS and auxins in the pre-culture and the co-cultivation phase could increase the infection rate further. Leaf explants from commercial *E. dunnii* clone DUN00003 were pre-cultured either on regeneration medium with the combination of 250 µM AS and elevated amount of auxin (2 mg/l IAA vs. 0.1 mg/l NAA in regeneration medium). Explants were pre-cultured for 4 days and then the explants are infected with *Agrobacterium* strain GV2260 containing pARB1001, which contains GUS gene (driven by a constitutive promoter) and NPTII gene (driven by a different constitutive promoter). Fifty explants were assayed for transient GUS expression following 4 days of pre-culture and 3 days of co-cultivation. Two hundred explants were selected on regeneration medium supplemented with 30 mg/l Geneticin and 400 mg/l timentin. At three months of selection on regeneration medium, the explants with callus surviving the selection were stained for GUS expression.

TABLE 13

| | | | | | | | |
|---|---|---|---|---|---|---|---|
| *E. dunnii* clone DUN00003 leaf explants | | | | | | | |
| Pre-culture Medium (EucReg Medium + PGR in mg/l) | No. Explants | No. GUS+ | % GUS+ | No. GUS Foci | No. Callus Lines | No. Solid GUS | No. Partial GUS |
| 5.0 zeatin/ 2 IAA + 250 µM AS | 50 | 50 | 100 | Large GUS foci fused | 59 | 18 | 29 |

Example 17

This example compares two combinations of AS and auxins in the pre-culture and the co-cultivation phase. Leaf explants from commercial *E. dunnii* clone DUN00001 were cultured on either regeneration medium with the combination of 250 µM AS and an elevated amount of auxin (either IAA at 2 mg/l IAA or 2,4-D at 0.25 mg/l) or regeneration medium with 0.1 mg/l NAA. Explants were pre-cultured for 4 days and then infected with *Agrobacterium* strain GV2260 containing pARB1001, as described in Example 16. Fifty explants from each treatment were assayed for transient GUS expression after 4 days of pre-culture and 3 days of co-cultivation.

TABLE 14

| | | | | | |
|---|---|---|---|---|---|
| *E. dunnii* clone DUN00001 leaf explants | | | | | |
| Pre-culture Medium (EucReg Medium + PGR in mg/l) | No. Explants | No. GUS+ | % GUS+ | No. GUS Foci | Avg. No. Foci/ Responding Explant |
| 5.0 zeatin/ 2 IAA + 250 µM AS | 49 | 45 | 91.8 | 311 | 6.9 |
| 5.0 zeatin/ 0.25 2,4-D + 250 µM AS | 49 | 34 | 69.4 | 125 | 3.7 |

Example 18

This example compares the infection of either leaf or internodal explants with two *Agrobacterium* strains, GV2260 and EHA105. The pre-culture and co-cultivation medium are the regeneration medium with the combination of 250 µM AS and an elevated amount of auxin as IAA at 2 mg/l IAA (vs. 0.1 mg/l NAA in regular regeneration medium). Leaf explants and 5 mm internodes were harvested from stock cultures of commercial *E. dunnii* clone DUN00003 and were cultured on the pre-culture medium as described in Example 4. Explants were pre-cultured for 4 days and then infected with either *Agrobacterium* strain GV2260 or strain EHA105 containing pARB1001. Fifty explants from each treatment were assayed for transient GUS expression after 4 days of pre-culture and 3 days of co-cultivation.

TABLE 15

| | | | | | |
|---|---|---|---|---|---|
| *E. dunnii* clone DUN00003 leaf explants | | | | | |
| Explant type/ Agrobacterium strain | No. Explants | No. GUS+ | % GUS+ | No. GUS Foci | Avg. No. Foci/ Responding Explant |
| Internodes/EHA | 40 | 27 | 67.5 | 239 | 8.9 |
| Internodes/GV2260 | 50 | 46 | 92 | 378 | 8.2 |
| Internodes/EHA | 50 | 34 | 68 | 342 | 10.0 |
| Internodes/GV2260 | 50 | 34 | 68 | 264 | 7.8 |

Example 19

Transformation of Early Flowering *Eucalyptus occidentalis*

This example details the infection and transformation of three early flowering *Eucalyptus* occidentalis clones EO66, EO129, and EO208 using the inventive transformation method. Leaf explants were harvested and pre-cultured for 4 days and then the explants were infected with *Agrobacterium*. strain GV2260 harboring p35SGUSINT (35S::GUSINT, NOS::NPTII). For EO66, the *Agrobacterium* strain was GV2260 harboring p35SGUSINT (35S::GUSINT, NOS:: NPTII). For EO129 and EO208, the *Agrobacterium* strain was the same GV2260, but the construct was pWVK192 (the promoter of pine 4CoA ligase driving the GUS gene with an intron—4CL::GUSINT, constitutive::NPTII). The explants were pre-cultured on regeneration medium with a modification that the $NH_4H_2PO_4$ was changed to 0.5 g/l instead of 0.25 g/l. The medium contained 750 µM AS and no elevated auxin concentration. Transient GUS expression data was collected after the pre-culture and co-cultivation steps. For EO66, transient GUS expression data was collected after the pre-culture and co-cultivation steps. There was no transient GUS expression data collected for EO129 and EO208. 144, 400 and 200 explants from clones EO66, EO129 and EO208, respectively, were transplanted to selection medium as regular regeneration medium with 30 mg/l Geneticin. After six months, regenerated shoots were stained for GUS expression and the results are shown in Table 16.

TABLE 16

Transformation of early flowering *E. occidentalis* clone EO66

| Clone | Pre-treatment Medium (EucReg Medium) | No. Explants | No. GUS+ | % GUS+ | No. GUS Foci | Total No. Starting Explants | GUS+ Shoot Lines | Transformation Rate (%) |
|---|---|---|---|---|---|---|---|---|
| EO66 | With 250 µM AS + 0.25 NH$_4$H$_2$PO$_4$ mg/l | 20 | 17 | 85 | 130 | 144 | 2 | 1.4 |
| EO129 | With 250 µM AS + 0.25 NH$_4$H$_2$PO$_4$ mg/l | ND | ND | ND | ND | 400 | 29 | 7.3 |
| EO208 | With 250 µM AS + 0.25 NH$_4$H$_2$PO$_4$ mg/l | ND | ND | ND | ND | 200 | 17 | 8.5 |

Example 20

Transformation of Elite Clones of Several *Eucalyptus* Species

This example provides transformation of elite clones. Explants from elite clones were prepared as described in Example 4 and are pre-cultured on medium comprising auxin and *Agrobacterium* inducer. The explants were transformed with *Agrobacterium* and co-cultivated as described in Example 5. Following co-cultivation and selection of transformants, the transformed explants were transferred to a shoot regeneration media as detailed in Example 6. Upon confirmation of GUS expression, the shoots were harvested and transferred to a rooting medium. Rooting is done on BTM-1 medium supplemented with 5 g/l MeadWestvaco Nuchar activated carbon, and the rooting occurs usually after 2-4 weeks. Once the root system has developed, the transformant was transferred to soil.

TABLE 17

| Species | Elite Clones Tested | Clones Transformed *(Plant Regeneration) |
|---|---|---|
| *E. grandis* | 4 | 3 |
| *E. grandis* x *urophylla* | 1 | 1 |
| *E. grandis* x *saligna* | 1 | 1 |
| *E. camaldulensis* | 1 | 1 |

Example 21

RT-PCR to Assess Expression of Herbicide Tolerance Gene

This example shows the presence and expression of a herbicide tolerance gene in a sample of transgenic lines. As described in Example 8, RNA was isolated from the leaves and stem tissues of each putative transgenic line. In particular, RNA was isolated from transformed *E. grandis*, *E. grandis*× *urophylla*, and *E. camadulensis* lines. In addition, RNA was isolated from wild-type *E. grandis*, *E. grandis*×*urophylla*, and *E. camadulensis* plants. For each line, a 5 µl RNA sample was used for RT-PCR to assess the presence and the expression of a herbicide tolerance gene. RT-PCR was performed with the Ready-to-Go RT-PCR kit (Pharmacia), according to the manufacturer's instructions. Briefly, each 5 µl RNA preparation was added to separate RT-PCR reactions containing oligo(dT)$_n$ and herbicide-resistant gene primers. Following RT-PCR, the amplification products were visualized on an ethidium bromide-stained agarose gel.

Agarose gel electrophoresis of the RT-PCR products revealed that all of the tested transgenic *Eucalyptus* lines express the herbicide tolerance gene. Specifically, all ten *E. grandis* lines analyzed for the presence of the herbicide tolerance gene expressed the herbicide tolerance gene, whereas the wild-type *E. grandis* plants do not. In addition, all eight of the *E. grandis*×*urophylla* express, while the control plants do not express ALS. Four transgenic *E. camadulensis* lines are analyzed for ALS expression, all of which express ALS. No herbicide tolerance gene expression was detected in any of the control plants.

Example 22

This example demonstrates the adaptability of the present transformation methodology to a different selectable marker, neomycin phosphotransferase (NPTII) gene, which confers resistance to aminoglycoside antibiotics neomycin, kanamycin or geneticin (G418). Leaf explants of commercial *E. grandis*×*urophylla* clone IPB1 were infected with *Agrobacterium* strain GV2260 harboring pWVC33, which contains GUS gene (driven by an constitutive promoter) and NPTII gene (driven by a different constitutive promoter). Before transforming, the explants were pre-cultured for 4 days on a medium having auxin enrichment (IAA at 2 mg/l instead of 0.1 mg/l NAA in standard regeneration medium) and acetosyringone (250 µM). As described in Example 6, the explants were infected with *Agrobacterium*, co-cultivated on the same medium for 3 days, and then transferred to a regeneration medium supplemented with 400 mg/l timentin for 4 days. Then, the explants were transferred to a selection medium containing geneticin instead of an herbicide selection agent.

The transformants were placed on geneticin selection medium containing geneticin (either 20 or 30 mg/l). Instead of the 3- or 4-week transfer cycles used with an herbicide selection medium, the explants were transferred bi-weekly to fresh geneticin medium. After about 10 weeks of growth on geneticin selection medium, samples of geneticin-resistant calli were collected and stained with x-gluc for GUS expression, as described in Example 7. The following data summarizes GUS expression in geneticin-selected transformants.

TABLE 18

Transformation of *Eucalyptus grandis* x *urophylla* Clone IPB1 with antibiotic selectable marker (NPTII)

| Concentration of Geneticin (mg/l)/ | Light Conditions for cultures | No. Explants | No. Calli Stained | No. GUS+ Calli |
|---|---|---|---|---|
| 20 | Regular shaded light | 162 | 5 | 0 |
| 30 | Regular shaded light | 162 | 17 | 13 |
| 30 | Dark | 162 | 6 | 4 |

Example 23

This example demonstrates that *Eucalyptus* explants can be transformed with *Agrobacterium* strain GV2260 harboring p35SGUSINT (35S::GUSINT, NOS::NPTII). Similar to the methods disclosed in Example 16, *E. camaldulensis* clone C9 was transformed with GV2260 harboring p35SGUSINT. Following regeneration, the explants were transferred to a selection medium containing geneticin (30, 40, 50, or 60 mg/l geneticin). For geneticin at levels of 30 and 50 mg/l, additional sets of explants were pre-cultured for 1 day. After 8 weeks on selection medium, samples of geneticin-resistant shoot cultures in the early developmental stage were collected and stained with x-gluc for GUS expression. GUS expression data is summarized in the following table.

TABLE 19

Transformation of *E. camaldulensis* clone C9 with antibiotic selectable marker (NPTII)

| Concentration of Geneticin (mg/l) | Length of Pre-culture (Days) | No. Explants | No. Shoot Lines Stained | No. GUS+ Shoot Lines | % GUS+ Shoots |
|---|---|---|---|---|---|
| 30 | 4 | 181 | 39 | 5 | 12.8 |
| 40 | 4 | 176 | 68 | 8 | 11.8 |
| 50/ | 4 | 178 | 31 | 7 | 19.4 |
| 60 | 4 | 182 | 8 | 4 | 50 |
| 30 | 1 | 180 | 29 | 11 | 37.9 |
| 50 | 1 | 181 | 12 | 6 | 50 |

GUS positive shoot lines were produced consistently from all treatments. Higher concentration of geneticin and shorter pre-culture time produced transgenic lines with limited escapes.

Example 24

This example demonstrates that a commercial *E. grandis* clone can be transformed with *Agrobacterium* strain GV2260 harboring another construct pWVR8. (*Arabidopsis* ActinII.:GUSINT, constitutive::NPTII). As described in Example 4, leaf explants from *E. grandis* clone IP1 were pre-cultured on a pre-culture medium comprising auxin and an *Agrobacterium* inducer. The explants were transformed with *Agrobacterium* and co-cultivated for 3 days on a pre-culture medium with auxin enrichment (IAA at 2 mg/l, instead of 0.1 mg/l NAA in standard regeneration medium) and acetosyringone (250 μM). Then the explants were transferred to Euc Regeneration medium supplemented with 400 mg/l timentin for 4 days. The explants were then transferred to selection medium containing geneticin (30 or 40 mg/l geneticin). After 8 weeks on selection medium, samples of geneticin-resistant shoot cultures in the early developmental stage were collected and stained with x-gluc for GUS expression. GUS expression data is summarized in Table 20.

TABLE 20

Transformation of *E. grandis* clone IP1 with antibiotic selectable marker (NPTII)

| Explant Source | Concentration of Geneticin (mg/l) | No. Explants | No. Shoot Lines Stained | No. GUS+ Shoot Lines | % GUS+ Shoots |
|---|---|---|---|---|---|
| Shoot cluster | 30 | 198 | 16 | 8 | 50 |
| Rooted plants | 30 | 198 | 1 | 0 | 0 |
| Shoot cluster | 40 | 198 | 7 | 4 | 57 |

Example 25

Based on the data from the above examples, elite *Eucalyptus* clones can be transformed with a foreign DNA by the disclosed method. For example, elite *Eucalyptus* clones can be transformed with a gene that encodes an enzyme involved in cellulose synthesis, such as a cellulose synthase. Cellulose synthase binds UDP-glucose and transfer the sugar to the non-reducing end of the nascent glucan chain. Using the methods of the present invention, the UDP-glucose binding domain can be overexpressed in a transgenic plant.

The transformation of *Eucalyptus* elite clones with a sense UDP-glucose binding domain sequence operably-linked to a constitutive promoter confers an enhanced growth phenotype, as evidenced by increases in cellulose synthesis, wood density, and tensile strength. Leaf explants are harvested from stock *Eucalyptus* plants and the explants are cultured on a pre-culture medium. The pre-culture medium comprises auxin, cytokinin, and an *Agrobacterium* inducer, such as acetosyringone, to stimulate cell division along the excised edges of the tissue explant. Following four days of pre-culture, the explants were inoculated with *Agrobacterium* strain GV2260 containing a plasmid bearing a portion of the GS coding region operably linked to the constitutive promoter. The explants were co-cultivated for 3 days before transfer to Euc Regeneration medium. The explants were cultured on Euc Regeneration medium for 4 days before transfer to selection medium containing an herbicide.

Following the selection of herbicide-resistant transformants, the transformants were assayed for GUS expression. Upon the confirmation of GUS expression, shoots were harvested and transferred to a rooting medium. The rooting medium comprises BTM- 1 salts supplemented with 5 g/l activated carbon, and rooting development usually occurs after 2-4 weeks. Upon development of the primary root system, the transformed plants are transferred to soil.

Example 26

Evaluation of ALS/Sulfonylurea in Selecting Transgenic Plants

This example describes the selection of genetically transformed pine, using a selectable marker encoding ALS on selection media containing a sulfonylurea herbicide, at a level sufficient for selection in model plants. In some experiments, including the one described in the following example, a vector that would express the als gene in the plant tissue was co-bombarded into the cells with a vector that would express the nptII gene in the plant tissue, and the co-bombarded cells were then divided into two groups and placed onto selection medium containing either a sulfonylurea herbicide or Geneticin, so that the frequency with which transformants are selected on Geneticin could be compared with the frequency of selection on herbicide.

Loblolly pine (*Pinus taeda*) and hybrid pine (*P. taeda*×*P. rigida*) embryogenic cell lines were initiated from zygotic embryos of individual immature megagametophytes using the procedures described in U.S. Pat. No. 5,506,136. Immature seed cones were collected from breeding orchards near Charleston, S.C. when the dominant zygotic embryo is at the precotyledonary stage of development. Using the classification system of von Arnold and Hakman (*J. Plant Phys.*, 132: 164-169 (1988)), the dominant zygotic embryo at this stage is referred to as being at stage 2; that is, an embryo with a prominent embryonic region with a smooth and glossy surface, subtended by elongated suspensor cells which are highly vacuolated. However, zygotic embryos at an earlier stage of development (stage 1) may also be used effectively to initiate embryogenic cultures.

For culture initiation, intact seeds removed from seed cones were surface sterilized with 10 to 20% commercial bleach solution (equivalent of a 0.525% to 1.050% sodium hypochlorite solution) for 15 minutes followed by three sterile water rinses (each of five minutes duration). The intact megagametophyte (which contains the developing zygotic embryos) was then removed from the seed coat and nuclear membranes, and placed on DCR1 or WV5$_1$ initiation medium.

Basal salt mixtures effective for pine embryogenesis culture initiation include, but are not limited to, the DCR or WV5 basal salts formulations listed in Table 21. Complete media formulations used for initiation, maintenance and proliferative growth of pine embryogenic cultures in this, and later examples, are listed in Table 22. The pH of the medium was adjusted to 5.8 with KOH and HCl prior to autoclaving at 110 kPa (16 psi) and 121° C. for 20 minutes. Those skilled in plant tissue culture will recognize that many other sterilization conditions can be used with the present method.

TABLE 21

Basal Culture Media Formulations For Pine Embryogenesis

| COMPONENT | WV5[a] | DCR[b] | MSG[c] |
|---|---|---|---|
| | CONCENTRATION (mg/L) | | |
| INORGANIC SALTS | | | |
| $NH_4NO_3$ | 700.00 | 400.00 | 0 |
| $KNO_3$ | 259.00 | 340.00 | 100.00 |
| $Ca(NO_3)_2 \cdot 4H_2O$ | 963.00 | 556.00 | 0 |
| $MgSO_4 \cdot 7H_2O$ | 1850.00 | 370.00 | 370.00 |
| $KH_2PO_4$ | 270.00 | 170.00 | 170.00 |
| $CaCl_2 \cdot 2H_2O$ | 0 | 85.00 | 440.00 |
| KCl | 1327.00 | 0 | 745.00 |
| KI | 0.83 | 0.83 | 0.83 |
| $H_3BO_3$ | 31.00 | 6.20 | 6.20 |
| $MnSO_4 \cdot H_2O$ | 15.16 | 22.30 | 16.90 |
| $ZnSO_4 \cdot 7H_2O$ | 8.60 | 8.60 | 8.60 |
| $Na_2MoO_4 \cdot 2H_2O$ | 0.25 | 0.25 | 0.25 |
| $CuSO_4 \cdot 5H_2O$ | 0.25 | 0.25 | 0.03 |
| $CoCl_2 \cdot 6H_2O$ | 0.03 | 0.03 | 0.03 |
| $NiCl_2 \cdot 6H_2O$ | 0 | 0.03 | 0 |
| $FeSO_4 \cdot 7H_2O$ | 27.80 | 27.80 | 27.80 |
| $Na_2EDTA$ | 37.30 | 37.30 | 37.30 |
| VITAMINS, AMINO ACIDS | | | |
| Nicotinic acid | 0.50 | 0.50 | 0.50 |
| Pyridoxine·HCl | 0.50 | 0.50 | 0.10 |
| Thiamine HCl | 1.00 | 1.00 | 0.10 |
| Glycine | 2.00 | 2.00 | 0 |
| Glutamine[d] | 0 | 250.00 | 1450.00 |

[a]According to Coke (1996).
[b]According to Gupta and Durzan (1985).
[c]According to Becwar et al. (1990).
[d]Added as a filter-sterilized aqueous stock to autoclaved medium while still warm (about 60° C.).

TABLE 22

Initiation, Maintenance, And Proliferation Media For Pine Embryogenesis

| COMPONENT | Gelled Initiation Medium WV5$_1$ | Gelled Initiation Medium DCR$_1$ | Gelled Maintenance Medium WV5$_2$ | Gelled Maintenance Medium DCR$_2$ | Preparation Medium DCR$_3$ | Liquid[f] Proliferation Medium DCR$_4$ |
|---|---|---|---|---|---|---|
| Basal medium[a] | WV5 | DCR | WV5 | DCR | DCR | DCR |
| | Concentration (g/L) | | | | | |
| Inositol | 0.50 | 0.50 | 0.50 | 0.50 | 0.50 | 0.50 |
| Casein hydrolysate[b] | 0.50 | 0.50 | 0.50 | 0.50 | 0.50 | 0.50 |
| L-glutamine | 0 | 0.25 | 0 | 0.25 | 0.25 | 0.25 |
| Sucrose | 0 | 30.00 | 30.00 | 30.00 | 0-60.00 | 30.00 |
| Maltose | 30.00 | 0 | 0 | 0 | 0-60.00 | 0 |
| Polyethylene glycol | 0 | 0 | 0 | 0 | 0-70.00 | 0 |
| GELRITE[c] | 1.5 | 1.5 | 2.00 | 2.00 | 0-6.00 | 0 |
| Activated Carbon | 0 | 0 | 0 | 0 | 0-0.5 | 0-0.5 |
| PHYTOHORMONES | | | | | | |
| | Concentration (mg/L) | | | | | |
| Auxin[d] | 1.0-3.0 | 3.0 | 1.0-3.0 | 3.0 | 3.0 | 3.0 |

TABLE 22-continued

Initiation, Maintenance, And Proliferation Media For Pine Embryogenesis

| COMPONENT | Gelled Initiation Medium WV5$_1$ | Gelled Initiation Medium DCR$_1$ | Gelled Maintenance Medium WV5$_2$ | Gelled Maintenance Medium DCR$_2$ | Preparation Medium DCR$_3$ | Liquid[f] Proliferation Medium DCR$_4$ |
|---|---|---|---|---|---|---|
| Cytokinin[e] | 0.50 | 0.50 | 0.50 | 0.50 | 0.50 | 0.50 |
| Abscisic Acid | 10.00 | 10.00 | 10.00 | 10.00 | 0 | 0 |

[a] Refer to Table 19 for composition of basal medium.
[b] In some of the Examples below, defined amino acid mixtures are substituted for casein hydrolysate.
[c] GELRITE ® (gellan gum manufactured by Merck, Inc.).
[d] 2,4-dichlorophenoxyacetic acid (2,4-D) or naphthalene acetic acid (NAA).
[e] N$^6$-benzylaminopurine (BAP) or N$^6$-benzyladenine (BA).
[f] For all gelled media, approximately 10, 15 or 20 ml of medium is poured into each 100 × 15 mm sterile plastic petri dish, and media is refrigerated or stored at room temperature until use. For all liquid culture media, no gelling agent is added and the medium is stored in 500 ml batches under refrigeration or frozen prior to use.

The perimeter of each petri dish was sealed with two wraps of NESCOFILM® (commercially available from Karlan Company). The dishes were incubated in the dark at a constant temperature of 23° C.±2° C. After about 7 to 21 days, embryogenic tissue was extruded from the micropyle of the megagametophyte explants. At six weeks, following the placement of the explant on initiation media, tissue masses extruding and proliferating from individual explants were isolated to individual petri plates on maintenance medium DCR$_2$ or Wv5$_2$ Individuals were assigned line numbers.

After one to three months of culture on maintenance medium, the tissue cultures were cryopreserved. Specifically, the cells were added to an equal volume of liquid DCR medium containing sorbitol, for a final concentration of 0.2-0.4M sorbitol. Aliquots of the cryoprotectant dimethyl sulfoxide (DMSO) were added to the suspension on ice to bring the final concentration of DMSO to 10%. One milliliter aliquots of the cell suspension containing DMSO were then transferred to freezing vials, placed in a programmable freezer, and cooled to −35° C. at 0.33° C. per minute. The freezing vials were subsequently immersed in liquid nitrogen inside a cryobiological storage vessel for long-term storage. Those skilled in the art of plant tissue culture will recognize that other cryopreservation protocols would be applicable to the present method.

Frozen cultures were retrieved for experimental use by removing individual vials from the cryobiological storage vessel and placing the vials in 42°±2° C. water to rapidly thaw the frozen cell suspensions. The thawed cell suspensions were aseptically poured from the cryovial onto a sterile polyester membrane support (cut from a bolt of polyester fabric commercially available from Sefar, catalog number PeCap® Catalog No. 7-35/11) placed over sterile filter paper (Whatman no. 2, Whatman International Ltd.) for a few minutes to allow the DMSO cryoprotectant solution to diffuse away from the embryogenic tissue into the paper. The embryogenic tissue on the polyester support membrane was then transferred to DCR$_2$ maintenance medium and incubated at 23° C. in the dark for 24 hours to allow additional DMSO to diffuse away from the tissue into the medium. The polyester support bearing the embryogenic tissue was then removed from the medium and transferred to fresh DCR$_2$ maintenance medium, and thereafter, every 14-21 days to a fresh plate until the amount of cells per plate reaches about 1 g. The culture environment during post-cryopreservation recovery and growth was 23° C.±2° C. in the dark. Those skilled in the art will recognize that many different cryopreservation and recovery procedures can be used with this method and that the detail in this example may not be construed to limit the application of the method.

Three embryogenic lines, from three different families (two genetically diverse loblolly pine families and a family of a loblolly x pitch pine hybrid), were used for the experiment. Uniform suspension cultures from each of the genetically different tissue culture lines were established by inoculating a 250 ml Nephelo sidearm flask (Kontes Chemistry and Life Sciences Products) with 1 g of tissue each into 20 ml liquid DCR4 medium. The flasks containing the cells in liquid medium are placed on a gyrotory shaker at 100 rpm in a dark culture room at a temperature of 23° C.±2° C. One week later, the liquid in each flask was brought to 35 ml by pouring 15 ml fresh medium into the culture flask and swirling to evenly distribute the cells. Cell growth was measured in the sidearm by decanting cells and medium into the sidearm portion of the flasks, allowing the cells to settle for 30 minutes and then measuring the settled cell volume (SCV). When the SCV is greater than or equal to half the maximal SCV (50% of the volume of the flask was occupied by plant cells), each culture was transferred to a 500 ml sidearm flask containing a total of 80 ml cells and medium and the transferred culture is maintained under the same conditions.

Twenty identical replicates from the suspension cells of each of these three pine lines were prepared for gene transfer according to the method described in U.S. Pat. No. 6,518,485. Polyester membrane supports of a defined weight were sterilized by autoclaving and placing in separate sterile Buchner funnels, and approximately 1.5 ml of uniform pine embryogenic suspension at SCV 30 was pipetted onto each support such that the embryogenic tissue was evenly distributed over its surface. Next, the liquid medium was suctioned from the tissues using a mild vacuum and each support bearing the embryogenic tissue was placed on a Gelrite® solidified DCR$_3$ preparation medium (Table 20) in 100×25 mm plastic petri dishes, which are incubated in a dark growth chamber at 23° C.±2° C. for about 24 hours. DNA is then transferred into the tissues and/or embryos via carrier particle (microprojectile) bombardment technology using the PDS-1000/He BIOLISTICS® Particle Delivery System (available from Bio-Rad Laboratories). The DNAs of interest, here equimolar amounts of vectors containing respectively the visual marker gene uidA and the potential selectable marker als, and the selectable marker nptII, were precipitated onto the surface of gold microparticles. The petri dishes with the fabric support and embryonic tissues were then placed into the interior of the PDS 1000/He BIOLISTICS® device and a vacuum was applied to a level of 28 inches Hg. Gold particles carrying 1 µg DNA were accelerated toward each plate of embryogenic tissue following a helium build-up and bursting regulated by a 1550 psi rupture disk. In the PDS-1000/He BIOLISTICS® device the gap between the rupture disk and the macrocarrier (gap distance) was 5 mm and the macrocarrier travel distance was 13 mm. Following DNA transfer the petri dishes containing the fabric support and tissues were incubated in a dark growth chamber at 23° C.±2° C. for about 24 hours. The tissues and fabric support were then transferred to semi-solid maintenance medium, $DCR_1$ (Table 20) to recover from carrier particle bombardment and incubated in a dark growth chamber at 23° C.±2° C. for a period of 5 days. At this point, one plate per cell line was sacrificed for GUS staining (an inserted uidA gene, encoding a β-glucuronidase enzyme expressing in tissue culture cells, was detected by deep blue staining of cells from each of the transgenic lines upon exposure to a colorigenic glucuronidase enzyme substrate, "X-gluc," commercially available from Inalco, according to techniques well known in the art of plant transformation) and microscopic examination, which demonstrates that cell division has resumed and that transient expression of the uidA transgene displays the normal frequency for these bombardments.

The remaining tissues were then transferred on their fabric support to a selection medium, semi-solid maintenance medium $DCR_1$ containing a level of selection agent inhibitory to the growth of non-transformed cells. In this example, one half of the replicates were placed on a selection medium containing Geneticin (commercially available from Gibco/ BRL) at 15 mg/L, and the other half is placed on a selection medium containing 50 nM Oust® (commercially available from DuPont™). The plates were incubated in a dark growth chamber at 23° C.±2° C. and the fabric supports bearing the tissues were transferred to the fresh culture medium of the same composition every 3 weeks.

Active growth on the selection medium occurs in a number of isolated sectors on many of the petri dishes. Such active growth in the presence of selection agent is normally an indication that the growing tissues have integrated the selection gene into their chromosomes and are stably transformed. These areas of active growth are treated as independent transformation events and are henceforth referred to as putative transgenic sublines. The putatively transgenic embryogenic tissue was multiplied by transferring growing transgenic sectors to fresh semi-solid maintenance $DCR_2$ medium supplemented with the respective selection agent. Any actively growing putatively transgenic embryogenic tissue was transferred to fresh semi-solid maintenance selection medium at 3 week intervals for a period of about six to twelve weeks depending on the rate of growth of the individual sublines of the transgenic embryogenic tissue.

Stable transformation is verified in 100% of the 12 putative transgenic sublines tested that are selected on Geneticin, through a combination of growth on selection medium, assay for expression of the visual marker gene, and polymerase chain reaction (PCR) amplification of specific segments of the transgene DNA sequence. These techniques were performed using techniques well known to those skilled in the art of molecular biology. Eighty percent of the putative transgenic sublines that are tested and selected on Oust are false positives.

Example 27

Evaluation of Casein Hydrolysate on the Selectivity of Sulfonylurea

Six embryogenic lines, two each from three different families (two genetically diverse loblolly pine families and a family of a loblolly x pitch pine hybrid), were evaluated. Uniform suspension cultures from each of the genetically different tissue culture lines were established as described in Example 26. Three identical replicates from the suspension cells of each of these six lines were plated as described in Example 26 on each of ten formulations of $DCR_2$ medium, namely with and without casein hydrolysate, and containing the herbicide Oust at 0, 10, 20, 40, and 80 nM. The plates were sealed and incubated under the same conditions used for pre-experimental initiation, maintenance and selection steps in Example 26. Every three weeks the culture was transferred to fresh medium of the same formulation as previously provided, following weighing under sterile conditions of the tissue on the polyester support. The growth on these media for each of the six cell lines after a total of twelve weeks is shown in FIG. 9.

Figure 9:
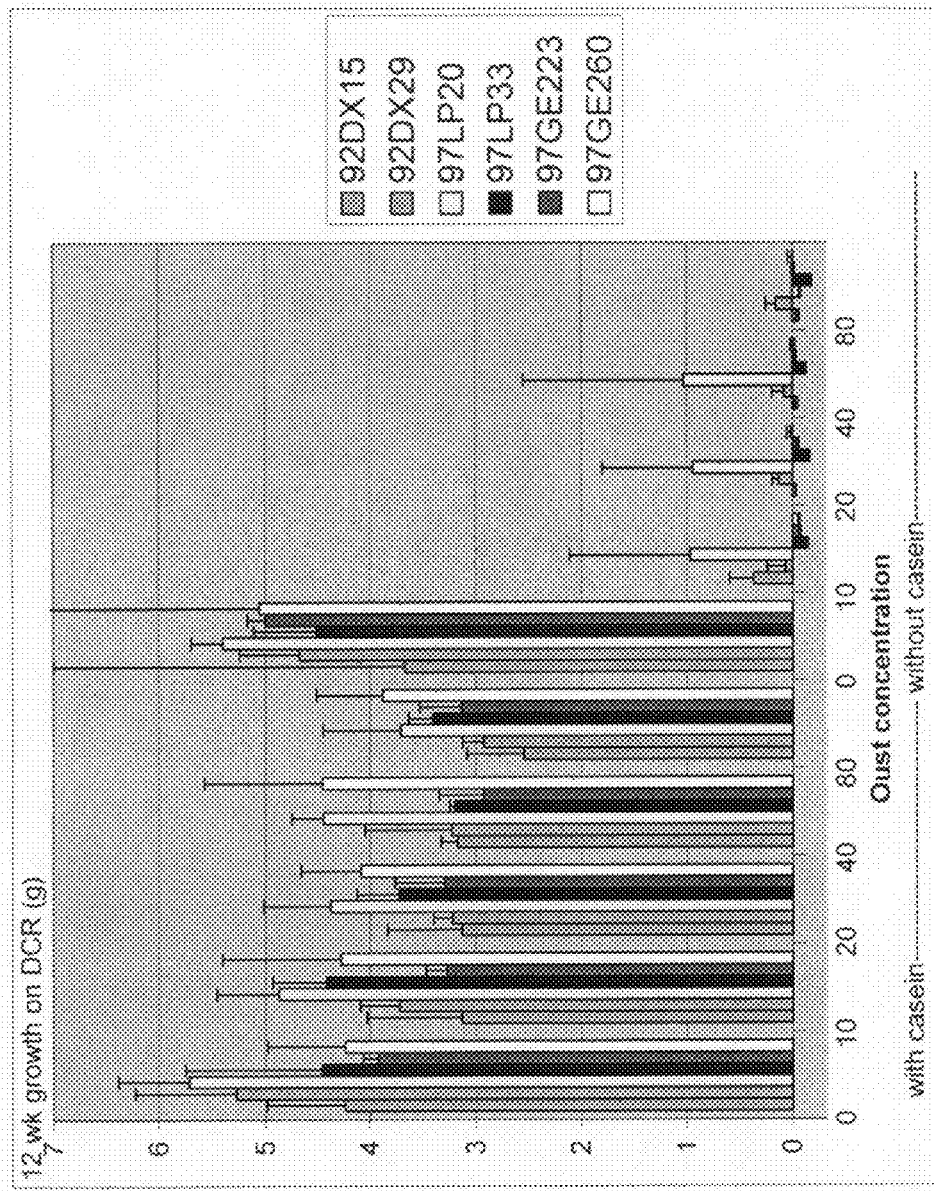
FIG. 9 presents graphical data showing the impact of casein hydrolysate on the herbicidal effects of sulfonylurea or imidazolinone.

FIG. 9 shows that sulfonylurea herbicide Oust is successful as a selective agent at multiple concentrations only in the absence of casein hydrolysate.

Stopping the growth of the cells using any concentration of the sulfonylurea herbicide Oust, which is what would be desirable if the herbicide was being used as a selective agent for transgenic cells, is not accomplished except in the absence of casein hydrolysate. Growth is retarded or stopped to a significant degree in the absence of casein hydrolysate simultaneously with the presence of Oust, which inhibits the biosynthesis of branched chain amino acids, suggesting that branched chain amino acid biosynthesis is active during growth of these cells and that the branched chain amino acids are indeed essential for growth. Contrary to the belief commonly held among those skilled in the art of plant tissue culture, cells were capable of growth without casein hydrolysate in the medium; however, some cell lines experienced reduced growth levels.

Further experimentation demonstrated that at least one of the lines has lost the potential to produce germinable embryos after maintenance on medium lacking casein that the same line exhibited after maintenance on medium containing casein. Also, two other lines displayed significantly reduced potential to produce germinable embryos after maintenance on medium lacking casein hydrolysate relative to the potential displayed after maintenance on medium containing casein hydrolysate. Potential to produce germinable embryos was measured as follows. After the cell masses that had been cultured on 0 nM Oust herbicide proliferate for twelve weeks, they were resuspended in $DCR_3$ liquid medium again. When the cell suspensions were brought to uniform (half-maximal) SCV, equivalent amounts of suspension culture cells were pipetted onto sterile membrane supports for placement on $MSG_1$ development/maturation medium as described in U.S. Pat. No. 5,506,136 (Table 23) to assess the ability of the cultures to develop high quality harvestable stage 3 (cotyledonary) embryos. Dishes were incubated in a dark growth chamber at 23±2° C. The membrane supports were transferred to new petri dishes containing fresh medium every 3 weeks. At week 9, stage 3 (cotyledonary) embryos were visually analyzed for germination quality.

TABLE 23

Development/Maturation And Germination
Media For Pine Embryogenic Cells

| COMPONENT | Development/ Maturation Medium $MSG_1$ | Pre-Germination Medium $MSG_2$ | Germination Medium $MSG_3$ |
|---|---|---|---|
| Basal medium[a] | MSG | MSG | MSG |
| | | CONCENTRATION (g/L) | |
| Ammonium Nitrate | 0 | 0 | 0.80 |
| Inositol | 0.10 | 0.10 | 0.10 |
| L-glutamine | 1.45 | 1.45 | 0 |
| Sucrose | 0 | 0 | 30.00 |
| Maltose | 60.00 | 60.00 | 0 |
| GELRITE[b] | 2.00 | 2.00 | 2.00 |
| Activated Carbon | 0-1.25 | 0 | 5.00 |
| PEG[c] | 0-100.00 | 0 | 0 |
| ABA[d] | 11-150 | 21 | — |

[a]Refer to Table 19 for composition of basal medium.
[b]GELRITE ® (gellan gum manufactured by Merck, Inc.).
[c]Polyethylene glycol (molecular weight of 4000).
[d]Abscisic acid.

Example 28

Evaluation of Sulfonylurea using Media without Casein Hydrolysate

In this example, five loblolly pine cell lines from four elite families were transformed with plasmids containing the als selectable marker, and selection was done on a sulfonylurea-containing selection medium modified to exclude casein hydrolysate. The five pine cell lines were initiated as described in Example 26, except that one of the five lines was an elite loblolly cross grown in an International Paper seed orchard in Georgia. The lines were cryopreserved, retrieved, and cultured as uniform suspensions as described in Example 26.

To prepare for gene transfer, polyester membrane supports were sterilized by autoclaving and placed in separate sterile Buchner funnels, and for each of six replicate plates per cell line, one to three milliliters of pine embryogenic suspension was pipetted onto each support such that the embryogenic tissue was evenly distributed. The liquid medium was suctioned from the tissues and each support bearing the embryogenic tissue was placed on gelled $DCR_3$ preparation medium for Agrobacterium inoculation according to the methods described in U.S. Patent Publication No. 20020100083. Specifically, binary constructs containing the als selectable marker were introduced into Agrobacterium tumefaciens by techniques well known to those skilled in the art, and virulence was induced with administration of acetosyringone by commonly used techniques whereupon the induced Agrobacterium was co-mingled with the plant material. The cells were co-cultivated in the dark at 22°±2° C. for approximately 72 hours.

Following co-cultivation, Agrobacterium was eradicated from the cultures. The cells were re-suspended into fresh DCR4 liquid wash medium (Table 20), containing 400 mg/L TIMENTIN®. Resuspension was initiated by grasping each membrane support bearing the infected cells, using forceps, and rolling it so that it can be placed into the liquid wash. The liquid was gently agitated to get the cells into suspension, and the membrane support was scraped with sterile forceps if cells adhere to it. Once the cells are in suspension, the membrane was removed.

Following each wash step, the cells were plated onto fresh sterile support membranes of the same type used in the previous step, again by placing the fresh sterile support membranes in a sterile Buchner funnel, pipetting the suspension of plant cells onto the membranes, and suctioning the liquid medium from the tissues using a mild vacuum. Additional washes were carried out until the medium drains from the cells clear. For each successive wash cycle, the cells were resuspended in fresh sterile wash medium by agitating the membrane bearing the cells in the liquid, removing cells that adhere by gently scraping with forceps. The cells were then re-plated on fresh membrane supports over Buchner funnels. Lines transformed with Agrobacterium and washed as described are plated onto gelled DCR media as described in Example 26, except that the media contains 10 mM ABA and 400 mg/L Timentin®. This recovery treatment was continued for one week. Cells borne on polyester membrane supports were then transferred onto the same medium except that it also contains no casein hydrolysate, and either 50 nM or 100 nm Ally® (DuPont™) for selection, and then transferred onto fresh selection media at intervals of 2 weeks. Seven putatively transformed sublines, after reaching approximately 2 g, were chosen for polymerase chain reaction (PCR) amplification for verification of the presence of transgenes using standard techniques. Primer pairs used for the reactions are shown below in Table 24.

TABLE 24

Primer Pairs for PCR

| | | Product size |
|---|---|---|
| virD2 | GAA GAA AGC CGA AAT AAA GAG G (SEQ ID NO: 1) | 560 |
| virD2 | TTG AAC GTA TAG TCG CCG ATA G (SEQ ID NO: 2) | |
| | These primers were used to check contamination by Agrobacterium | |
| NptII | AAG GAG ATA TAA CAA TGA TTG AAC AAG ATG GAT TGC (SEQ ID NO: 3) | 800 |
| NptII | TCA GAA GAA CTC GTC AAG AAG G (SEQ ID NO: 4) | 800 |
| uid(gus) | CGA AAA CGG CAA GAA AAA GCA G (SEQ ID NO: 5) | 450 |
| uid(gus) | ACG ACC AAA GCC AGT AAA GTA G (SEQ ID NO: 6) | |
| Pal | AAT GGG AAG CCT GAG TTT ACA (SEQ ID NO: 7) | 700 |
| Pal | GGC CAG CAT GTT TTC CTC CAG (SEQ ID NO: 8) | |
| | These primers, for the PAL gene, were used as a positive control | |

TABLE 24-continued

Primer Pairs for PCR

| | | Product size |
|---|---|---|
| Als | AAG ATA TTC AAC AAC AGC (SEQ ID NO: 9) | 1000 |
| Als | CCC GAG AAA TGT GTG AGC (SEQ ID NO: 10) | |
| Als | TAA CCC CGT CTT CCT CAA TCC (SEQ ID NO: 11) | 720 |
| Als | AAA CGC CAA CAA CAA ATC ACT (SEQ ID NO: 12) | |

For the detection of the ALS gene, two sets of primers were used, which were designed so as not to result in a product from the resulting wild type pine gene. A putatively transformed subline was confirmed as a transgenic if the primers for the pine PAL gene give a positive control product, the primers for the virD gene give no product, indicating no remaining contaminating *Agrobacterium*, and primers for the appropriate transgenes yield products. Six of the seven transformants tested were positive, indicating a false positive rate of only 14% as a result of the improved selection conditions used in this example as compared to Example 26. This demonstrates that the absence of casein selection methods are sufficient for selecting transformed cells using the als selectable marker and the sulfonylurea herbicide as a selection agent.

However, the transgenic cells selected in this experiment were slow-growing and did not appear sufficiently healthy to differentiate harvestable, regenerable embryos. Thus, it is clear that the improved selection method, wherein casein hydrolysate is omitted, is not sufficient to support a useful regeneration system, and further improvements are needed for normal growth and development of the embryogenic cells.

Example 29

Preparation of Vectors with Selectable Markers ALS or ASA2

DNA vectors were designed that contain a reporter gene and the nptII selectable marker as well as the alternative selectable markers als or asa2 driven by constitutive promoters. The relative positions of the genes in the vectors were designed such that in a binary vector, the selectable marker nptII would be near the border that is most often lost during transformation, and the alternative selectable marker would be between the nptII gene and the uidA reporter gene. This was done in order to allow for selection experiments in which the cells could be selected first or in parallel using nptII, and the presence of the nptII gene, as evidenced by successful geneticin selection, is evidence of a high likelihood that the alternative selectable marker linked between these two genes is present. This configuration facilitated testing and development of the selection system using rapid non-molecular measures of transformation success until alternative marker selection conditions were established. The vectors were designed so that convenient restriction sites allow the subsequent removal of the nptII and uidA genes, as well as the insertion of other genes of interest. The alternative selectable marker, positioned near the border that is most often lost during transformation, allows genes of interest to be co-transferred with the alternative selectable marker.

Figure 4:
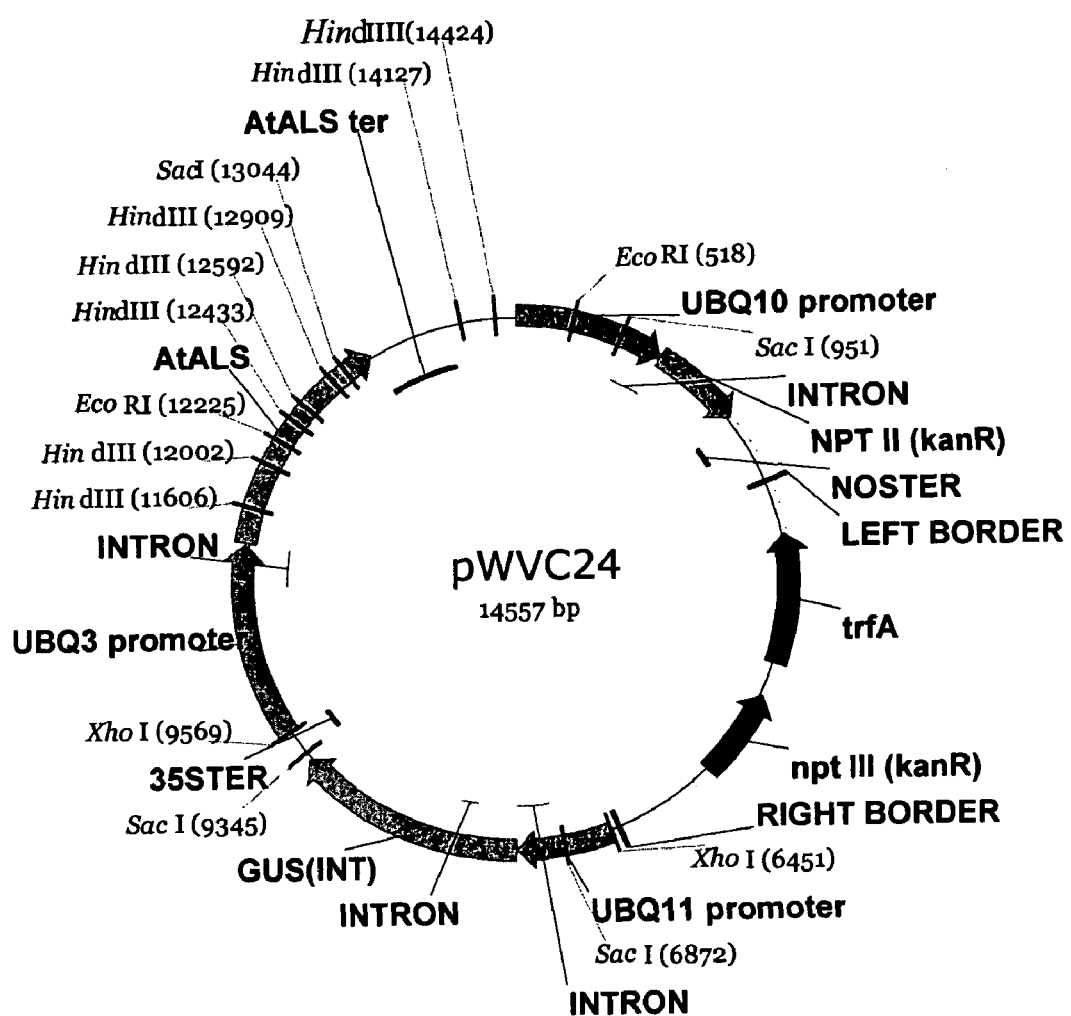
FIG. 4 provides a schematic representation of the vector pWVC24.

The als gene is pubicly known and available. GenBank contains numerous als genes from plants. For example, GenBank Accessions Nos. gi 30693053, gi 30685789, and gi 30685785 provide als genes isolated from *Arabidopsis thaliana*. While and als sequence may be used, the present invention used an als cassette subcloned, using SalI and SmaI, from pML1 (DuPont™). The als cassette was then cloned into the vector Bluescript™ (Stratagene) to make the construct pWVC20. (FIG. 1) The cassette was placed under the expression of a ubiquitin promoter subcloned using the restriction enzymes HindIII and NcoI from p2554 (Norris et al. 1993. *Plant Molecular Biology*, 21:895-906) to make pWVC22and provide additional restriction sites and allow for high copy accumulation. The larger (4.9 kb) als plant expression cassette, restricted with ApaI and NotI, was then inserted into binary vectors containing the nptII and uidA genes driven by different constitutive promoters, such that the als plant expression cassette is located between the nptII and uidA genes and flanked by convenient restriction sites, to give rise to pWVC23(FIG. 3) and pWVC24 (FIG. 4). Thus, it is straightforward to obtain pWVC25(FIG. 5a), containing only the uidA and als plant expression cassettes, and pWVC26 (FIG. 5b), containing only the als plant expression cassette, into which cassettes of interest can be cloned for insertion into plants using als selection. Such cassettes of interest can include, but are not limited to, genes that will add or increase the production of molecules of interest, such as syringyl lignin biosynthesis genes or stress resistance genes or RNAi or antisense constructs that decrease the production of molecules of interest.

The asa2 gene is publicly known and available. GenBank contains numerous asa2 genes from plants. For example, GenBank Accessions Nos. gi 4256949 and gi 3348125 provide asa2 genes isolated from plants. While any asa2 sequence may be used, the present invention used an asa2 gene subcloned from the plasmid pUC35SASA2 (Song, H. S. et al. (1998) *Plant Physiol.* 117:2:533-548) using the restriction enzymes SphI and BamHI to give a 4800 bp promoterless fragment for pWVC30 (FIG. 6) and was placed under the expression control of a ubiquitin promoter subcloned from p2554. This T4-ligated cassette was cloned into the Bluescript™ vector pBSKII+ to provide two additional restriction sites, ApaI and NotI. These restriction enzymes were used to cut out a 3800 bp fragment, which was ligated into a binary vector containing the nptII and uidA genes driven by different constitutive promoters, as described above, to produce pWVC33 (FIG. 7). The asa2 plant expression cassette is located between the nptII and uidA genes and flanked by additional convenient restriction sites.

Thus, it is straightforward to obtain pWVC34(FIG. 8a), containing only the uidA and asa2 plant expression cassettes, and pWVC35 (FIG. 8b), containing only the asa2 plant expression cassette, into which cassettes of interest may be cloned for insertion into plants using asa2 selection. Such cassettes of interest include, but are not limited to, genes that will add or increase the production of molecules of interest, such as syringyl lignin biosynthesis genes or stress resistance genes or RNAi or antisense constructs that decrease the production of molecules of interest.

The pWVC23 (FIG. 3), pWVC24 (FIG. 4) and pWVC33 (FIG. 7) plasmids were transformed into the *Escherechia coli* XL10-Gold bacterial competent cell line and the *Agrobacterium tumefaciens* cell line GV2260, using standard techniques.

Example 30

Two loblolly cell lines were prepared for transformation using the same methods of Example 28, and co-cultivated with *Agrobacterium tumefaciens* transformed with pWVC23 (FIG. 3), also as described in Example 28. Following eradication of *Agrobacterium*, each cell line was equally divided onto selection medium containing either Geneticin at 15 mg/L or Ally at either 50 or 100 nM. After putatively transformed sublines were grown to a sufficient size, nine sublines grown on Ally-containing media were transferred to Geneticin-containing media to check transformation status rapidly before PCR. 100% of these lines are able to grow on Geneticin-containing media. Five of these lines were then checked with PCR using the six primer pairs described in Example 28. 100% of these lines were confirmed postive transformants by PCR. However, these lines displayed the same non-regenerable phenotype as the lines described in Example 28.

In a similar experiment, five loblolly and hybrid pine lines were prepared for transformation using the methods in Example 28, except that one of the five lines initiated from cones collected from the Rigesa seed orchard in Tres Barras, Brazil. The lines were co-cultivated with *Agrobacterium* transformed with pWVC24 (FIG. 4) as described in Example 28. Following eradication of *Agrobacterium*, each cell line was equally divided onto selection medium containing either Geneticin at 15 mg/L or Ally at either 50, 75, 100 or 125 nM.

After eight weeks of selection, putatively transformed sublines have grown on Geneticin and on each of the four levels of Ally. Transformation was confirmed with GUS staining and PCR. However, these lines display the same non-regenerable phenotype as the lines described in Example 28.

Example 31

Preparation and Testing of Synthetic Casein Hydrolysate Mixtures

Casein hydrolysate is a complex mixture containing primarily free amino acids obtained by hydrolysis of the casein milk protein, but also some free ammonia and small amounts of dipeptides, tripeptides and more complex peptides. Table 23 below shows the free amino acid composition and free ammonia composition of casein hydrolysate as determined by analytical procedures cited in the Sigma® catalog for two different years.

TABLE 25

Trypsin Digest of Casein (Sigma C4523)
Typical free amino acid assay in mg/g casein

|  | 1990 list | 1993 list |
|---|---|---|
| Ammonia | 0.14 | 0.4 |
| Proline | 1.25 | 1.25 |
| Glycine | 1.99 | 1.99 |
| Aspartic acid | 2.31 | 2.31 |
| Cysteine | 2.5 | 2.5 |
| Alanine | 5.28 | 5.2 |

TABLE 25-continued

Trypsin Digest of Casein (Sigma C4523)
Typical free amino acid assay in mg/g casein

|  | 1990 list | 1993 list |
|---|---|---|
| Glutamic acid | 5.45 | 5.45 |
| Histidine | 5.85 | 5.85 |
| Threonine | 8.52 | 8.52 |
| Serine | 9.04 | 9.04 |
| Tryptophan | 12.12 | 12.2 |
| Tyrosine | 12.7 | 12.7 |
| Methionine | 13.2 | 13.2 |
| Valine | 18.3 | 18.3 |
| Phenylalanine | 25.7 | 25.7 |
| Arginine | 25.8 | 25.8 |
| Lysine | 50.8 | 50.8 |
| Leucine | 54 | 54 |
| iso-leucine | 72.4 | 72.4 |

In designing a synthetic casein hydrolysate, it was recognized that some of the components in natural casein hydrolysate promote plant cell growth and differentiation, while others have the opposite effect. Thus, it was important to replace only the components that are known to deter plant cell growth and differentiation. A variety of synthetic casein hydrolysate mixtures were prepared and are described in Table 26.

TABLE 26

Synthetic casein hydrolysate mixtures

| amino acid | mg/g in mixture AA1 | mg/g in mixture AA2 | mg/g in mixture AA3 | mg/g in mixture AA4 |
|---|---|---|---|---|
| glycine | 1.99 | 1.99 | 1.99 | 1.99 |
| threonine | 8.52 | 8.52 | 8.52 | 8.52 |
| serine | 9.04 | 9.04 | 9.04 | 9.04 |
| tryptophan | 12.2 | 12.2 | 0 | 0 |
| tyrosine | 12.7 | 12.7 | 0 | 12.7 |
| methionine | 13.2 | 13.2 | 13.2 | 13.2 |
| valine | 18.3 | 0 | 18.3 | 18.3 |
| phenylalanine | 25.7 | 25.7 | 0 | 25.7 |
| arginine | 25.8 | 25.8 | 25.8 | 25.8 |
| lysine | 50.8 | 50.8 | 50.8 | 50.8 |
| leucine | 54 | 0 | 54 | 54 |
| iso-leucine | 72.4 | 0 | 72.4 | 72.4 |

The synthetic mixtures were tested in 13 loblolly and hybrid pine lines from 7 genetically diverse families. These lines were initiated and cryopreserved as described in Example 26, and were placed into uniform suspension cultures and plated onto the respective media treatments as described in Example 27. Media for the experiment comprised $DCR_2$ maintenance media containing either 0.5 g/L casein hydrolysate, 0.5 g/L of one of the derived mixtures having the proportions shown in Table 24, or lacking both casein and the amino acid mixtures, and each of these treatments were provided with each of 0, 10, 30, or 50 mM treatments of the herbicide Ally® (commercially available from Dupont™). Growth data after six weeks was averaged across all 13 lines, as shown in FIG. 10.

Figure 10:
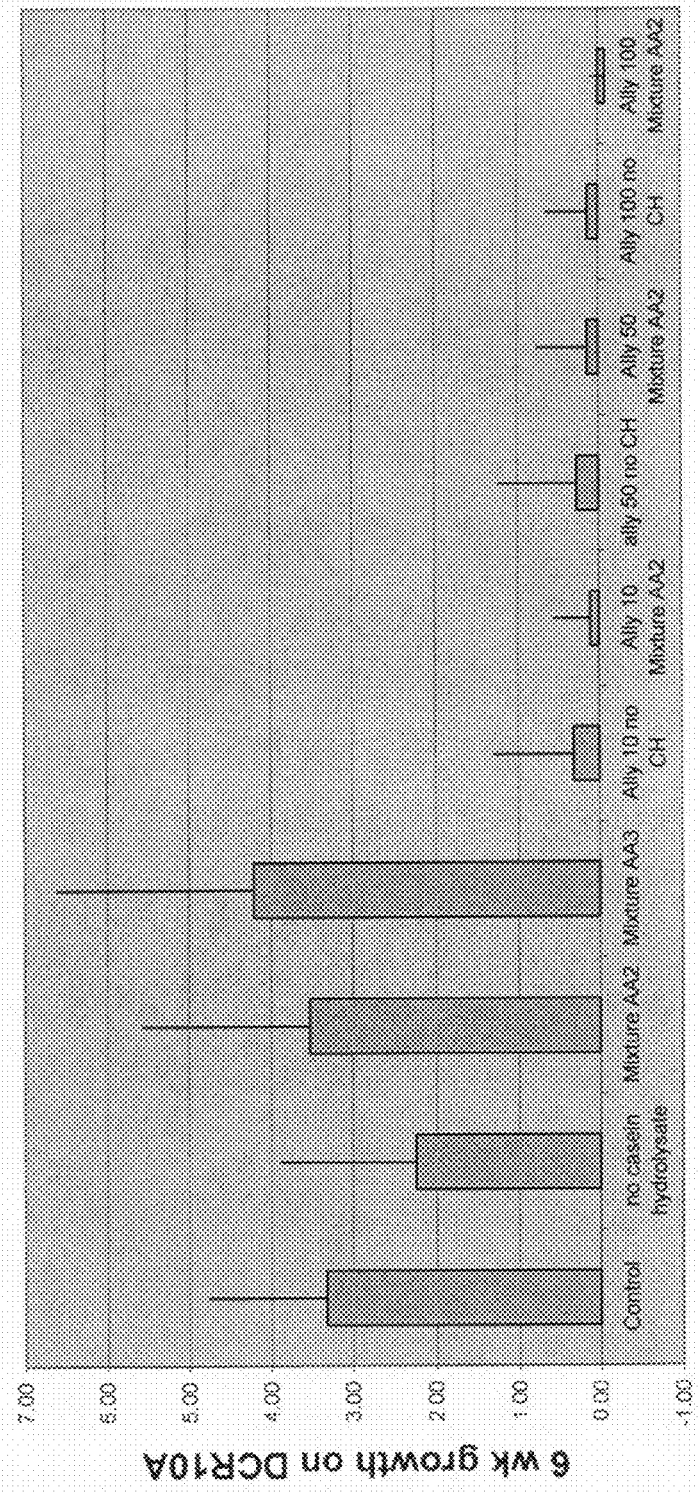
FIG. 10 depicts the herbicidal effect of a sulfonylurea in the presence of various compositions of casein hydrolysate.

FIG. 10 shows that the absence of casein hydrolysate reduces plant growth. Meanwhile, both synthetic mixtures support growth equal to or better than that achieved on medium containing casein hydrolysate. The results indicate that the growth requirement for casein hydrolysate is satisfied by synthetic replacements and that such replacements promote superior growth of embryogenic pine cultures.

In addition, the results show that growth is retarded or stopped to a significant degree on media containing an amino acid mixture in which branched chain amino acids are absent and which also contain the sulfonylurea herbicide Ally®. This confirms that branched chain amino acid biosynthesis are essential for growth. Furthermore, the data indicate that growth retardation of the cells by the sulfonylurea herbicide Ally®, is at least as effective in the presence of the mixture lacking branched chain amino acids as it is in the absence of casein hydrolysate.

In another experiment, 10 different loblolly and hybrid pine lines were used, from eight genetically diverse families. These lines were initiated and cryopreserved as described in Example 26, and were placed into uniform suspension cultures and plated onto the respective media treatments as described in Example 26. Media for the experiment comprised $DCR_2$ maintenance media containing either 0.5 g/L casein hydrolysate, 0.5 g/L of the derived mixture AA4 having the proportions shown in Table 24, or lacking both casein and the amino acid mixtures, and each of these treatments were provided with each of 0, 3, 10, or 30 mg/L treatments of 5-methyltryptophan (5MT). Transfers to fresh media was carried and weights were measured every 2-3 weeks at the times shown in FIG. 11. The vertical axis is the total weight increase in grams after the respective period.

Figure 11:
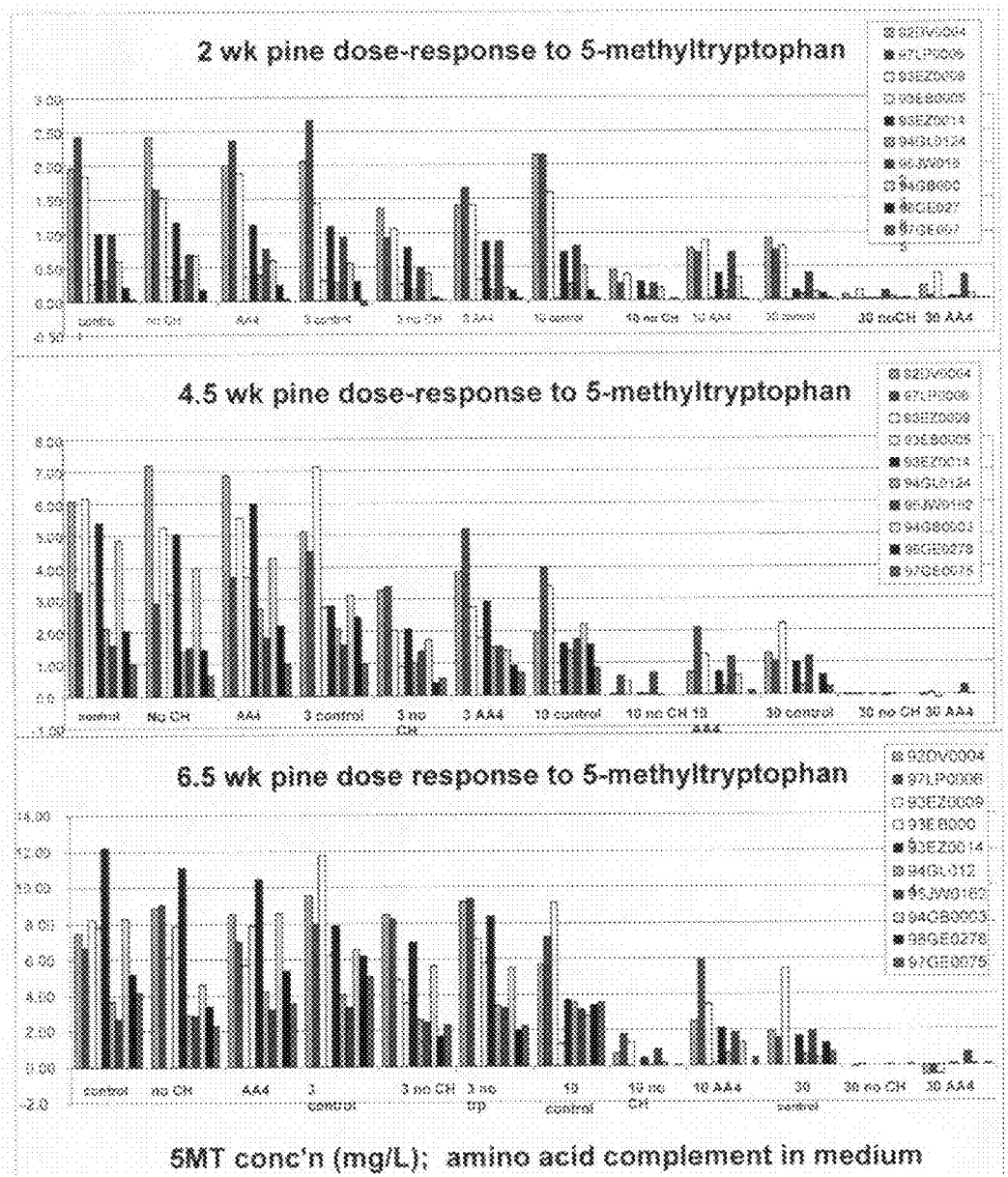
FIG. 11 shows the effect of tryptophan on the herbicidal effect of 5MT.

FIG. 11 shows that mixture AA4 is capable of replacing casein hydrolysate, and that only in the absence of tryptophan is it possible to obtain satisfactory reduction in growth with the application of 5-methyltryptophan. The data further show that within the first two weeks on medium lacking tryptophan and containing lethal levels of 5-methyltryptophan, some growth still occurs. This suggests that pre-depletion of amino acids, such as tryptophan in this case, obtained in the tissue from prior culture in normal casein-hydrolysate-containing medium provides an effective means for using a selectable marker that blocks an amino acid biosynthesis pathway.

Example 32

Evaluation of Delectivity of 5MT and AMT

Two loblolly cell lines were prepared for transformation using the method of Example 28, and co-cultivated with *Agrobacterium tumefaciens* transformed with pWVC33 (FIG. 7) as described in Example 28. Following eradication of *Agrobacterium*, each cell line was equally divided onto 6 plates each of 5 different selection media containing either casein hydrolysate and Geneticin at 15 mg/L, or amino acid mixture AA4 and either 5-methyltryptophan (5MT) at 30 or 50 mg/L or β-methyltryptophan (AMT) at 30 or 50 mg/L. The results are show in FIG. 12. Putatively transformed sublines grow on Geneticin-containing plates and on both selection treatments where 30 mg/L of the methylated tryptophan selective analog was incorporated.

After putative transformants are of sufficient size, they were checked by PCR using the nptII, uidA, VirD and PAL primer pairs described in Example 28 with the following primer pairs for asa2, designed specifically so that they do not give rise to a product from the pine native ASA2 gene.

TABLE 27

| Primer Pairs for PCR | | |
|---|---|---|
| | | Product size |
| asa2 | CTC GCA TTC TAT CTG TTC (SEQ ID NO: 13) | 731 |

TABLE 27-continued

| Primer Pairs for PCR | | |
|---|---|---|
| | | Product size |
| asa2 | AAC GCT TTG AGA GAA GA (SEQ ID NO: 14) | |
| asa2 | CTC GCA TTC TAT CTG TTC (SEQ ID NO: 13) | 478 |
| asa2 | CGC AGA GCA CAT CAT (SEQ ID NO: 15) | |
| asa2 | CTC GCA TTC TAT CTG TTC (SEQ ID NO: 13) | 1193 |
| asa2 | AGC CCA GAC TCA TTG A (SEQ ID NO: 16) | |

The PCR results are shown in Table 28 below. The rate of false positives is not significantly different between the selection treatments.

TABLE 28

| asa2 PCR Results | | | |
|---|---|---|---|
| | Geneticin | 5MT30 | AMT30 |
| PCR tested confirmed positive | 12 | 8 | 22 |
| False positive | 11 | 7 | 20 |
| Frequency | 0.08 | 0.13 | 0.09 |

Subsequent experiments tested depletion of the amino acids in the media before selection by providing casein-free preparation media and recovery media, or by providing the amino acid mixture AA4 in the preparation media and recovery media.

Example 33

Figure 7:
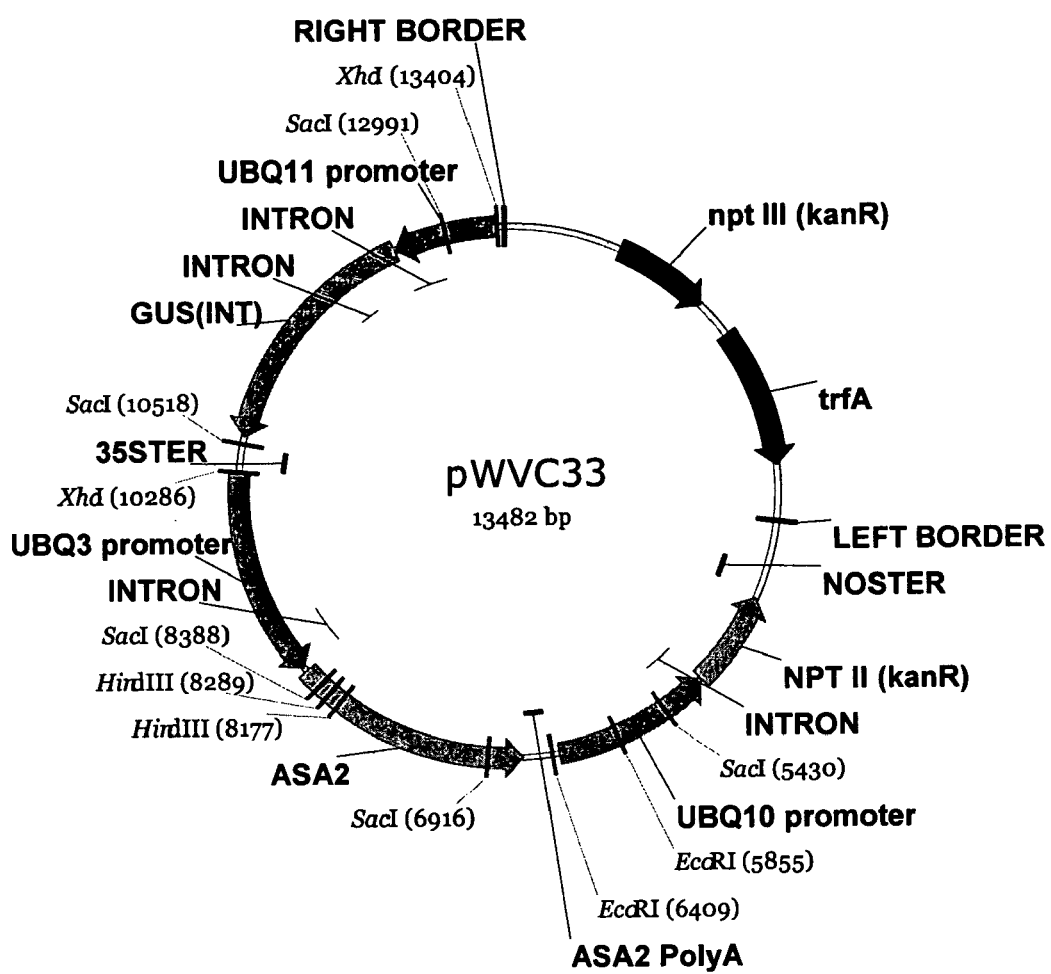
FIG. 7 provides a schematic representation of the vector pWVC33.
Figure 8A:
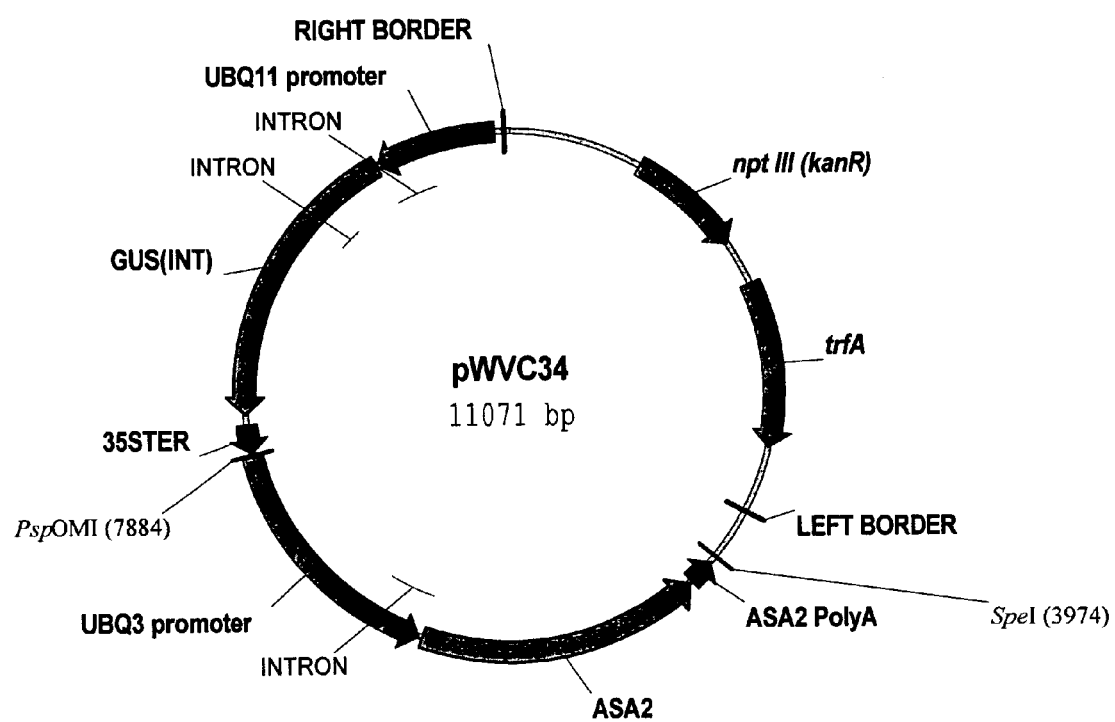
FIG. 8a provides a schematic representation of the vector pWVC34 and FIG. 8b provides a schematic representation of the vector pWVC35 .
Figure 8B:
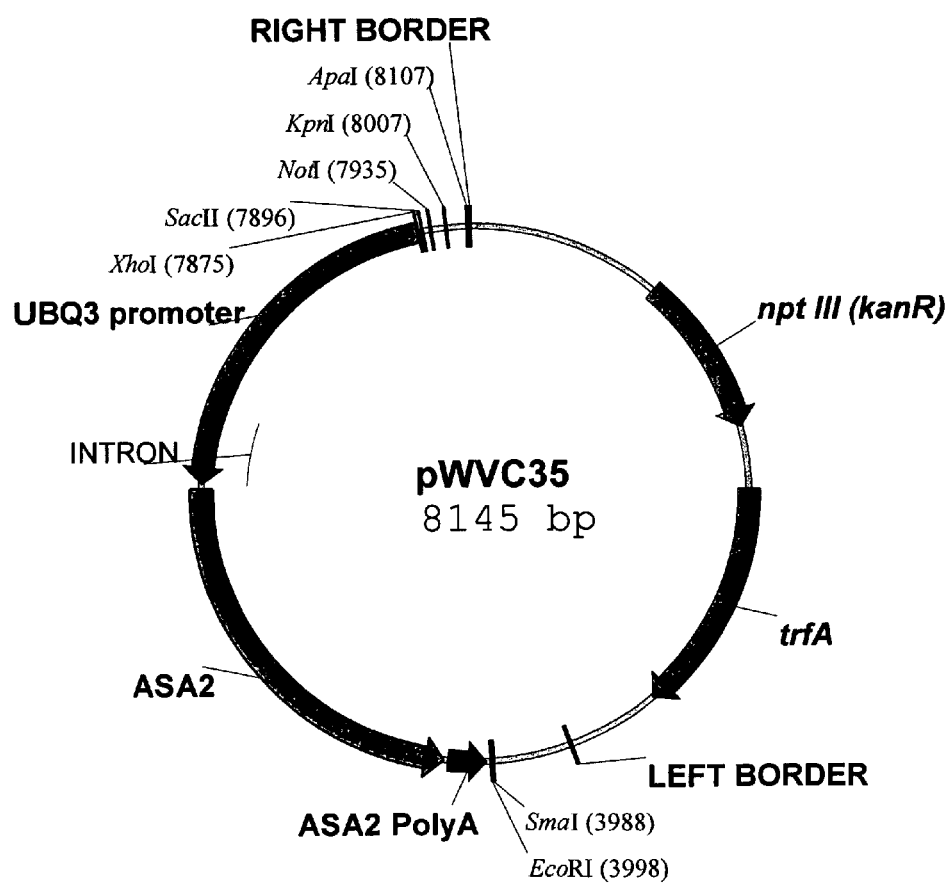

In this experiment, six genetically diverse loblolly and hybrid pine lines, including a Brazilian loblolly pine line from an elite family as in Example 30, were prepared for transformation and co-cultivated as in Example 28, splitting cells of each line between *Agrobacterium* strains transformed with pWVC24 (FIG. 4) or pWvC33 (FIG. 7).

Cells from each line were washed and plated on recovery medium lacking casein hydrolysate so that there is a one-week depletion of branched chain amino acids and tryptophan. Cells were split across selection treatments in which the basal salts are varied, using either DCR or Mi3 (Table 27). This demonstrated that the modifications made to the selection media in Examples 30-33 do not work differently in different basal salt formulations, but are applicable in any salt formulation known to those skilled in woody plant tissue culture. Transformants with pWVC24 (FIG. 4) are recovered from Geneticin selection media and Ally selection media on both salt formulations. Transformants with pWVC33 (FIG. 7) were recovered from Geneticin selection media and α-methyltryptophan selection media on both salt formulations. Transformants using a control plasmid, not containing either als or asa2, were recovered from Geneticin selection media on both salt formulations. The results show that the modifications made to the selection media in Examples 30-33 did not work differently in different basal salt formulations, and are applicable in any salt formulation known to those skilled in woody plant tissue culture.

TABLE 29

Mi3 Maintenance Medium formulation in mg/liter and molar (mM) concentrations

| Component | mg/liter | molecular wt.(g) | mM conc. | % (molar) of total |
|---|---|---|---|---|
| NH4NO3 | 200 | 80.04 | 2.499 | 2.990 |
| KNO3 | 910 | 101.11 | 9.000 | 10.769 |
| Ca(NO3)2 4H2O | 236 | 276.23 | 0.854 | 1.022 |
| MgSO4 7H2O | 247 | 246.48 | 1.002 | 1.199 |
| Mg(NO3)2 6H2O | 257 | 280.73 | 0.915 | 1.095 |
| MgCl2 6H2O | 102 | 203.31 | 0.502 | 0.600 |
| KH2PO4 | 136 | 136.09 | 0.999 | 1.196 |
| MnSO4 H2O | 10.5 | 169.01 | 0.062 | 0.074 |
| ZnSO4 7H2O | 14.7 | 287.54 | 0.051 | 0.061 |
| CuSO4 5H2O | 0.173 | 249.68 | 0.001 | 0.001 |
| KI | 4.16 | 166.01 | 0.025 | 0.030 |
| CoCl2 6H2O | 0.125 | 237.93 | 0.001 | 0.001 |
| H3BO3 | 15.5 | 61.83 | 0.251 | 0.300 |
| Na2MoO4 2H2O | 0.125 | 241.95 | 0.001 | 0.001 |
| FeSO4 7H2O | 27.8 | 278.02 | 0.100 | 0.120 |
| Na2EDTA 2H2O | 37.3 | 374.26 | 0.100 | 0.119 |
| THIAMINE•HCL | 1 | 337.30 | 0.003 | 0.004 |
| PYRIDOXINE•HCL | 0.5 | 169.18 | 0.003 | 0.004 |
| NICOTINIC ACID | 0.5 | 123.00 | 0.004 | 0.005 |
| GLYCINE | 2 | 75.07 | 0.027 | 0.032 |
| Inositol | 500 | 180.16 | 2.775 | 3.321 |
| Sucrose | 15,000 | 342.30 | 43.821 | 52.432 |
| Casein Hydrolysate[a] | 500 | mole. wt. ? | ? | ? |
| L-glutamine | 3,000 | 146.15 | 20.527 | 24.561 |
| 2,4-D | 3 | 221.04 | 0.014 | 0.016 |
| BA | 0.5 | 225.25 | 0.002 | 0.003 |
| ABA | 10 | 264.32 | 0.038 | 0.045 |
| Gelling Agent[b] | 3000 | mole. wt. ? | — | — |
| total[c]: | | | 83.576 | 100.000 |

[a]Sigma C4523
[b]PhytaGel from Sigma P-8169
[c]Total does not include casein of unknown molecular weight The transformed cells were then plated onto differentiation medium as described in Example 27, to obtain germinable embryos. Harvestable embryos were collected in approximately equal numbers from nptII transformants cultured on Geneticin, pWVC24 transformants cultured on Ally, and WvC33 transformants cultured on α-methyltryptophan.

Harvested embryos are matured, converted into acclimatized plants, and prepared for field planting. Embryos on fabric supports were transferred to medium $MSG_3$ (Table 21), and incubated for about four weeks in the dark at a temperature of 4° C.±2° C. Next, embryos on their fabric supports were incubated above water in sealed containers for about three weeks in the dark at a temperature of 25° C.±2° C. Following the above two treatments, embryos on their fabric supports were transferred to medium $MSG_4$ (Table 21) and incubated for about three days in the dark at a temperature of 25° C.±2° C. Embryos were then removed from their fabric supports and placed onto the surface of fresh $MSG_4$ medium for germination. Germination was conducted in the light at a temperature of 25° C.±2° C. Germination plates were examined weekly, over a period of about four weeks, and germinating embryos were transferred to MAGENTA® boxes containing 100 ml of $MSG_4$ medium for conversion to plantlets. MAGENTA® boxes containing developing plantlets were incubated in the light at 25° C.±2° C. for about eight to twelve weeks.

When the plantlets form epicotyls (newly formed shoots of approximately two to four cm), they were transferred to containers filled with a potting mix [2:1:2 peat:perlite:vermiculite, containing 602 g/m$^3$ OSMOCOTE fertilizer (18-6-12), 340 g/m$^3$ dolomitic lime and 78 g/m$^3$ MICRO-MAX micronutrient mixture (Sierra Chemical Co.)]. The plantlets were grown in a shaded greenhouse and misted infrequently for a period of about two weeks. They were removed from mist for acclimatization in the greenhouse for about four weeks. Plantlets were then transferred to outdoor shade for about six weeks for final acclimatization before moving to full-sun conditions.

Although a significantly lower proportion of pWVC24 transgenic lines produced embryos that survived maturation, the percentage of lines surviving to planting on soil was similar in all treatments to control germination.

TABLE 30

| Sample | Mature Embryos | Germinating Embryos |
|---|---|---|
| non-transgenic control | 100% | 100% |
| Selected using als | 50% | 100% |
| Selected using asa2 | 92% | 86% |
| Selected using nptII | 93% | 100% |

This inventive selection method has generated at least ten plants per line from several dozen pine lines stably transformed with either als or asa2 that will be planted in an operationally prepared field site under an APHIS notification later this year.

This is the first reported successful use of these selection agents and these selectable markers in pine transformation that produced regenerable pine plants. Accordingly, this selection method can be used for selecting diverse transgenic trees.

What is claimed is:

1. A transformed explant regeneration medium comprising a sulfonylurea or imidazolinone herbicide and a derivative of casein hydrolysate, wherein said medium is free of branched chain amino acids and casein hydrolysate, and wherein said derivative of casein hydrolysate consists of glycine, threonine, serine, tryptophan, tyrosine, methionine, phenylalanine, arginine, and lysine.

2. A method for producing a transgenic plant, comprising (i) pre-culturing an explant on a medium comprising an inducer of *Agrobacterium*; (ii) exposing said explant to an *Agrobacterium* strain harboring a vector capable of transferring a gene to a plant cell; (iii) selecting a transformed explant on the regeneration medium of claim 1; and (iv) regenerating a transgenic plant from said explant.

3. A transformed explant regeneration medium comprising a tryptophan analog and a derivative of casein hydrolysate, wherein said regeneration medium is free of tryptophan and casein hydrolysate, and wherein said derivative of casein hydrolysate consists of glycine, threonine, serine, tyrosine, methionine, valine, phenylalanine, arginine, lysine, leucine, and isoleucine.

4. A method for selecting a transformed tree explant cell comprising, (i) transforming a tree explant cell with a vector comprising a gene encoding a herbicide-resistant form of plant acetoacetate synthase (ALS) and a gene involved in lignin biosynthesis or cellulose synthesis, and (ii) growing said transformed tree explant cell on the medium of claim 1.

5. A method of selecting a transformed tree explant cell comprising, (i) transforming a plant cell with a vector comprising a gene encoding a feedback-insensitive form of anthranilate synthase (AS) and a gene involved in lignin biosynthesis or cellulose synthesis, and (ii) growing said transformed tree explant cell on the regeneration medium of claim 3.

6. The transformed explant regeneration medium of claim 1, wherein the medium comprises 0.5 g/L of the derivative of casein hydrolysate and the derivative of casein hydrolysate consists of 1.99 mg/g glycine, 8.52 mg/g threonine, 9.04 mg/g serine, 12.2 mg/g tryptophan, 12.7 mg/g tyrosine, 13.2 mg/g methionine, 25.7 mg/g phenylalanine, 25.8 mg/g arginine, and 50.8 mg/g lysine.

7. The transformed explant regeneration medium of claim 3, wherein the medium comprises 0.5 g/L of the derivative of casein hydrolysate and the derivative of casein hydrolysate consists of 1.99 mg/g glycine, 8.52 mg/g threonine, 9.04 mg/g serine, 12.7 mg/g tyrosine, 13.2 mg/g methionine, 18.3 mg/g valine, 25.7 mg/g phenylalanine, 25.8 mg/g arginine, 50.8 mg/g lysine, 54 mg/g leucine, and 72.4 mg/g isoleucine.

8. A method for producing a transgenic plant, comprising (i) pre-culturing an explant on a medium comprising an inducer of *Agrobacterium*; (ii) exposing said explant to an *Agrobacterium* strain harboring a vector capable of transferring a gene to a plant cell; (iii) selecting a transformed explant on the regeneration medium of claim 3; and (iv) regenerating a transgenic plant from said explant.

9. The method of claim 8, wherein the transgenic plant is selected from the group consisting of: a transgenic *E. occidentalis* plant, a transgenic *E. dunnii* plant, a transgenic *E. grandis* plant, and a transgenic *E. grandis×E. urophylla* hybrid plant.

10. The method of claim 2, wherein the transgenic plant is selected from the group consisting of: a transgenic *E. occidentalis* plant, a transgenic *E. dunnii* plant, a transgenic *E. grandis* plant, and a transgenic *E. grandis×E. urophylla* hybrid plant.

* * * * *

SEQUENCE LISTING

<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaagaaagcc gaaataaaga gg                                            22

```
<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttgaacgtat agtcgccgat ag                                                  22

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaggagatat aacaatgatt gaacaagatg gattgc                                   36

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcagaagaac tcgtcaagaa gg                                                  22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgaaaacggc aagaaaaagc ag                                                  22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acgaccaaag ccagtaaagt ag                                                  22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aatgggaagc ctgagtttac a                                                   21

<210> SEQ ID NO 8
<211> LENGTH: 21
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggccagcatg ttttcctcca g                                              21

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aagatattca acaacagc                                                  18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cccgagaaat gtgtgagc                                                  18

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
taacccgctc ttcctcaatc c                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaacgccaac aacaaatcac t                                              21

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctcgcattct atctgttc                                                  18

<210> SEQ ID NO 14
<211> LENGTH: 17
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 14
aacgctttga gagaaga                                                    17

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgcagagcac atcat                                                      15

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agcccagact cattga                                                     16
```